United States Patent
De Groot et al.

(10) Patent No.: US 8,248,617 B2
(45) Date of Patent: Aug. 21, 2012

(54) INTERFEROMETER FOR OVERLAY MEASUREMENTS

(75) Inventors: Peter De Groot, Middletown, CT (US);
Jan Liesener, Middletown, CT (US);
Xavier Colonna De Lega, Middlefield, CT (US)

(73) Assignee: Zygo Corporation, Middlefield, CT (US)

( * ) Notice: Subject to any disclaimer, the term of this patent is extended or adjusted under 35 U.S.C. 154(b) by 260 days.

(21) Appl. No.: 12/427,079

(22) Filed: Apr. 21, 2009

(65) Prior Publication Data

US 2009/0262362 A1 Oct. 22, 2009

Related U.S. Application Data

(60) Provisional application No. 61/046,901, filed on Apr. 22, 2008.

(51) Int. Cl.
*G01B 11/02* (2006.01)
(52) U.S. Cl. .......................................... 356/508
(58) Field of Classification Search ................ 356/478, 356/508, 511
See application file for complete search history.

(56) References Cited

U.S. PATENT DOCUMENTS

| | | | |
|---|---|---|---|
| 5,216,257 A | 6/1993 | Brueck et al. | |
| 5,483,343 A | 1/1996 | Iwamoto et al. | |
| 5,783,342 A * | 7/1998 | Yamashita et al. | 430/30 |
| 7,230,705 B1 | 6/2007 | Yang et al. | |
| 7,428,057 B2 | 9/2008 | Colonna de Lega et al. | |
| 7,791,727 B2 * | 9/2010 | Den Boef et al. | 356/401 |
| 2003/0160968 A1 * | 8/2003 | Deck | 356/515 |
| 2004/0189999 A1 | 9/2004 | de Groot et al. | |
| 2005/0012928 A1 * | 1/2005 | Sezginer et al. | 356/401 |
| 2005/0134863 A1 * | 6/2005 | De Lega et al. | 356/512 |
| 2006/0015659 A1 | 1/2006 | Krantz et al. | |
| 2006/0158658 A1 | 7/2006 | Colonna de Lega et al. | |
| 2011/0032535 A1 * | 2/2011 | Liesener et al. | 356/511 |

FOREIGN PATENT DOCUMENTS

WO    WO 94/00733    1/1994

OTHER PUBLICATIONS

Kandel, Daniel et al., "Differential Signal Scatterometry Overlay Metrology: An Accuracy Investigation," Proc. Of SPIE, vol. 6616, pp. 66160H-1-66160H-11 (2007).

* cited by examiner

*Primary Examiner* — Tarifur Chowdhury
*Assistant Examiner* — Jonathan Hansen
(74) *Attorney, Agent, or Firm* — Fish & Richardson P.C.

(57) ABSTRACT

In general, in a first aspect, the invention features a system including an interferometer configured to direct test light to an overlay target and subsequently combine it with reference light to form an interference pattern, the test and reference light being derived from a common source, a multi-element detector, one or more optics to image the overlay target on the multi-element detector; and an electronic processor in communication with the multi-element detector. The overlay target includes a first pattern and a second pattern and the electronic processor is configured to determine information about the relative alignment between the first and second patterns.

24 Claims, 15 Drawing Sheets

INTERFEROMETER FOR OVERLAY MEASUREMENTS

CROSS-REFERENCE TO RELATED APPLICATIONS

This application claims benefit of Provisional Patent Application No. 61/046,901, entitled "INTERFEROMETER FOR OVERLAY MEASUREMENTS," filed Apr. 22, 2008, the entire contents of which are incorporated herein by reference.

BACKGROUND

The invention relates to interferometry, and to using interferometry for overlay measurements.

Interferometric techniques are commonly used to measure the profile of a surface of an object. To do so, an interferometer combines a measurement wavefront reflected from the surface of interest with a reference wavefront reflected from a reference surface to produce an interferogram. Fringes in the interferogram are indicative of spatial variations between the surface of interest and the reference surface.

A scanning interferometer scans the optical path length difference (OPD) between the reference and measurement legs of the interferometer over a range comparable to, or larger than, the coherence length of the interfering wavefronts, to produce a scanning interferometry signal for each camera pixel used to measure the interferogram. A limited coherence length can be produced, for example, by using a white-light source, which is referred to as scanning white light interferometry (SWLI). A typical scanning white light interferometry (SWLI) signal is a few fringes localized near the zero optical path difference (OPD) position. The signal is typically characterized by a sinusoidal carrier modulation (the "fringes") with bell-shaped fringe-contrast envelope. The conventional idea underlying SWLI metrology is to make use of the localization of the fringes to measure surface profiles.

SWLI processing techniques include two principle trends. The first approach is to locate the peak or center of the envelope, assuming that this position corresponds to the zero optical path difference (OPD) of a two-beam interferometer for which one beam reflects from the object surface. The second approach is to transform the signal into the frequency domain and calculate the rate of change of phase with wavelength, assuming that an essentially linear slope is directly proportional to object position. See, for example, U.S. Pat. No. 5,398,113 to Peter de Groot. This latter approach is referred to as Frequency Domain Analysis (FDA).

Scanning interferometry can be used to measure surface topography and/or other characteristics of objects having complex surface structures, such as thin film(s), discrete structures of dissimilar materials, or discrete structures that are underresolved by the optical resolution of an interference microscope. By "underresolved" it is meant that the individual features of the object are not fully separated in a surface profile image taken using the interference microscope as a consequence of the limited lateral resolution of the instrument. Surface topography measurements are relevant to the characterization of flat panel display components, semiconductor wafer metrology, and in-situ thin film and dissimilar materials analysis. See, e.g., U.S. Patent Publication No. US-2004-0189999-A1 by Peter de Groot et al. entitled "Profiling Complex Surface Structures Using Scanning Interferometry" and published on Sep. 30, 2004, the contents of which are incorporated herein by reference, and U.S. Patent Publication No. US-2004-0085544-A1 by Peter de Groot entitled "Interferometry Method for Ellipsometry, Reflectometry, and Scatterometry Measurements, Including Characterization of Thin Film Structures" and published on May 6, 2004, the contents of which are incorporated herein by reference.

Other techniques for optically determining information about an object include ellipsometry and reflectometry. Ellipsometry determines complex reflectivity of a surface when illuminated at an oblique angle, e.g. 60°, sometimes with a variable angle or with multiple wavelengths. To achieve greater resolution than is readily achievable in a conventional ellipsometer, microellipsometers measure phase and/or intensity distributions in the back focal plane of the objective, also known as the pupil plane, where the various illumination angles are mapped into field positions. Such devices are modernizations of traditional polarization microscopes or "conoscopes," linked historically to crystallography and mineralogy, which employs crossed polarizers and a Bertrand lens to analyze the pupil plane in the presence of birefringent materials.

Conventional techniques used for thin film characterization (e.g., ellipsometry and reflectometry) rely on the fact that the complex reflectivity of an unknown optical interface depends both on its intrinsic characteristics (material properties and thickness of individual layers) and on three properties of the light that is used for measuring the reflectivity: wavelength, angle of incidence, and polarization state. In practice, characterization instruments record reflectivity fluctuations resulting from varying these parameters over known ranges. Optimization procedures such as least-squares fits are then used to get estimates for the unknown parameters by minimizing the difference between measured reflectivity data and a reflectivity function derived from a model of the optical structure.

Interferometers having multiple modes for determining characteristics of an object are disclosed in US 2006-0158657 A1 (now U.S. Pat. No. 7,428,057) and US 2006-0158658 A1, the entire contents both of which are incorporated herein by reference.

SUMMARY

In one aspect, the disclosure relates generally to using interferometry for metrology during semiconductor processing, in which precise overlay registration (i.e., the relative orientation and position) of patterned layers is a fundamental requirement. Traditional methods of overlay registration include specially designed patterned features ("registration marks") that are easily resolved using a conventional imaging microscope. Common among these registration marks are, for example, the box-in-box features, which are analyzed using machine vision technology to determine overlay registration.

More recently, scatterometry has been applied to the overly registration problem. Conventionally, in these techniques, the directly-measured intensity of diffracted orders from superimposed grating-like registration marks reveal the overlay registration between layers.

Interferometric techniques for overlay measurements are described. In embodiments, an optical interferometric profiler is set up to generate signals representative of the 3D reflected intensity and phase profile of an object that includes two or more patterned layers stacked on top of each other. In certain embodiments, the same techniques can be applied where the two patterned layers are coplanar, such as in the context of double-exposure a resist or double-patterning of an integrated circuit layer. Processing of the interference signals generated by the profiler determines the overlay registration of the patterned layers with respect to each other.

In certain embodiments, the multiple patterned layers correspond to steps in a photolithography process. Patterning a resist layer in the process includes forming symmetric periodic structures (registration targets), either as a natural part of the photolithography process or specifically designed for the measurement. Examination of lateral asymmetry in the interference signals generated by the optical interferometric profiler reveals the overlay registration of the patterned layers with respect to each other.

We now summarize various aspects and features of the invention.

In general, in a first aspect, the invention features a system including an interferometer configured to direct test light to an overlay target and subsequently combine it with reference light to form an interference pattern, the test and reference light being derived from a common source, a multi-element detector, one or more optics to image the overlay target on the multi-element detector; and an electronic processor in communication with the multi-element detector. The overlay target includes a first pattern and a second pattern and the electronic processor is configured to determine information about the relative alignment between the first and second patterns.

Embodiments of the system can include one or more of the following features. For example, the system can further include a translation stage configured to adjust the relative optical path length between the test and reference light when they form the interference pattern. The system can also include a base for supporting a test object having the test surface, and wherein the translation is stage is configured to move at least a portion of the interferometer relative to the base. In some embodiments, the system includes the common source, wherein the translation stage is configured to vary the optical path length over a range larger than a coherence length for the common source.

The electronic processor can be configured to determine information about the relative alignment based on asymmetry between the interference pattern at different locations on the multi-element detector.

The first pattern can be a periodic pattern in at least a first dimension. In some embodiments, the first pattern is a grating having a first period. The second pattern can be a grating having a second period, either the same or different as the first period. The first period can be in a range from 50 nm to about 1,000 nm. In certain embodiments, the first pattern is also periodic in a second dimension, orthogonal to the first dimension. The pattern can have a period in the first and second dimensions that is the same or different. The second pattern can also be periodic in the first and/or second dimensions.

The interferometer can include a beam splitter configured to separate input light derived from the common source into the test light and the reference light, and a reference surface positioned to reflect the reference light before it is combined with the test light. The test light can be configured to reflect from the overlay target, and the beam splitter in the interferometer is positioned to recombine the test and reference light after they reflect from the respective test and reference surfaces.

The common source can be spatially extended. The system can further include the common source, wherein the common source can be a broadband source spanning more than 50 nm at full width half maximum. In some embodiments, the common source is a tunable source, the interferometer includes a reference surface positioned to reflect the reference light, and the reference surface is further positioned to produce a non-zero optical path length difference with the test light at the interference pattern.

The first pattern can be formed in a first layer of the overlay target and the second pattern can be formed in a second layer of the overlay target, the first layer being different from the second layer. In some embodiments, the first and second patterns are formed in a single layer of the overlay target.

In general, in another aspect, the invention features an interferometry method, that includes directing test light to an overlay target, subsequently combining the test light with reference light to form an interference pattern, wherein the test and reference light are derived from a common source and the overlay target comprises a first layer having a first pattern and a second layer having a second pattern, monitoring the interference pattern while varying an optical path difference between the test light and the reference light, and determining information about the relative alignment between the pattern of the first layer and the pattern of the second layer based on the monitored interference pattern.

Implementations of the interferometry method may include one or more of the following features. The information about the relative alignment is determined based on an asymmetry in the interference pattern. Determining the information can include determining a spatial frequency transform of an interference pattern. The transform can be a Fourier transform.

The information about the relative alignment can be determined in two orthogonal dimensions using first and second patterns that are composed of structures that are periodic in the two dimensions.

The method can be performed using an imaging interferometer and the first and second patterns can include features that have are underresolved by the imaging interferometer.

In general, in another aspect, the invention features a system that includes an interferometer configured to direct test light to an overlay target and subsequently combine it with reference light to form an interference pattern, the test and reference light being derived from a common source, a multi-element detector positioned to detect the interference pattern, and an electronic processor in communication with the multi-element detector. The overlay target includes a first pattern and a second pattern, the first and second patterns including features that are underresolved by the interferometer. The electronic processor is configured to determine information about the relative alignment between the features of the first and second patterns.

Embodiments of the system may include the following feature or one or more of the features disclosed with respect to other aspects. For example, the system can further include optics to image the overlay target on the multi-element detector.

In another aspect, the invention features a process for making a display panel, including providing a component of the display panel, the component supporting an overlay target, determining information about the overlay target using a system or method discussed above with respect to one of the foregoing aspects, and forming the display panel using the component based on the information about the overlay target. Implementations of the process can include one or more of the features discussed above in relation to other aspects of the invention.

In a further aspect, the invention features a process for making an integrated circuit, including providing a substrate comprising one or more integrated circuit structures, determining information about the one or more integrated circuit structures using a system or method discussed above with respect to one of the foregoing aspects, where the substrate includes the overlay target and the information is information about the overlay target, and forming the integrated circuit using the substrate based on the information. Implementations of the process can include one or more of the features discussed above in relation to other aspects of the invention.

Among other advantages, the methods and systems disclosed herein can provide accurate overlay measurements of relatively small target features (e.g., gratings having periods on the order of the wavelength of visible light or less, gratings that are underresolved by the apparatus used to make the measurement). The disclosed systems and methods can provide overlay measurements that are more accurate than overlay measurements made using a non-interferometric imaging microscope, for example.

As used herein, "light" is not limited to electromagnetic radiation in the visible spectral region, but rather refers generally to electromagnetic radiation in any of the ultraviolet, visible, near infrared, and infrared spectral regions.

Unless otherwise defined, all technical and scientific terms used herein have the same meaning as commonly understood by one of ordinary skill in the art to which this invention belongs. In case of conflict with any document incorporated by reference, the present disclosure controls.

Other features and advantages will be apparent from the following detailed description.

BRIEF DESCRIPTION OF THE DRAWINGS

Like reference numerals in different drawings refer to common elements.

DETAILED DESCRIPTION

Figure 1:
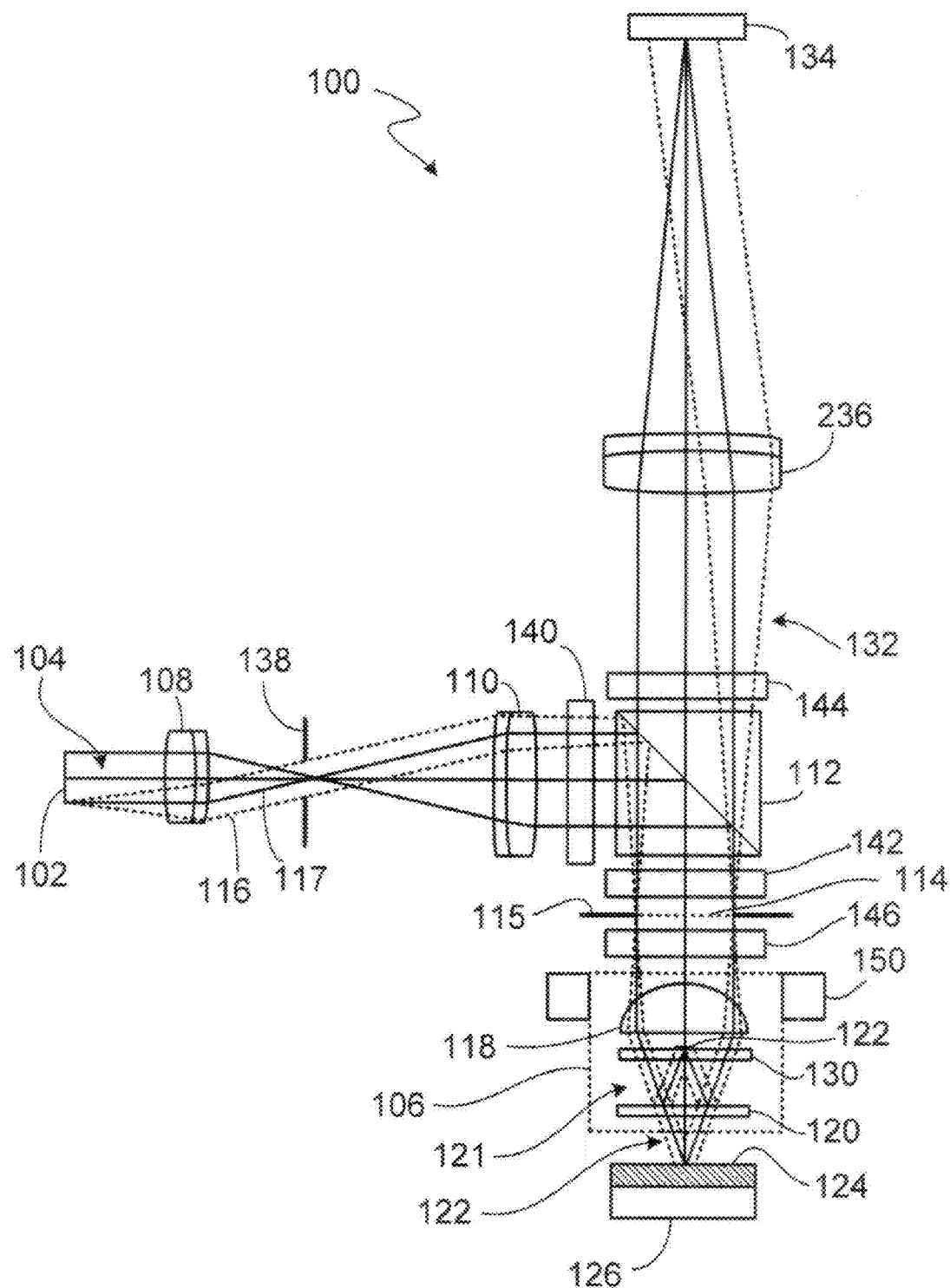
FIG. 1 is a schematic diagram of an interferometry system 100 configured to operate in a profiling/overlay mode.

Imaging interferometry systems are used for measuring overlay registration between two target structures. FIG. 1 shows an example of an interferometry system 100 that can be used for this purpose. Interferometry system 100 includes a spatially extended source 102 that directs input light 104 to an interference objective 106 via relay optics 108 and 110 and beam splitter 112. The relay optics 108 and 110 image input light 104 from spatially extended source 102 to an aperture stop 115 and corresponding pupil plane 114 of the interference objective 106 (as shown by the dotted marginal rays 116 and solid chief rays 117).

In the embodiment of the FIG. 1, interference objective 106 is of the Mirau-type, including an objective lens 118, beam splitter 120, and reference surface 122. Beam splitter 120 separates input light 104 into test light 121, which is directed to a test surface 124 of a test object 126, and reference light 128, which reflects from reference surface 122. Objective lens 118 focuses the test and reference light to the test and reference surfaces, respectively. The reference optic 130 supporting reference surface 122 is coated to be reflective only for the focused reference light, so that the majority of the input light passes through the reference optic before being split by beam splitter 120.

After reflecting from the test and reference surfaces, the test and reference light are recombined by beam splitter 120 to form combined light 132, which is transmitted by beam splitter 112 and relay lens 236 to form an optical interference pattern on an electronic detector 134 (for example, a multi-element CCD or CMOS detector). The intensity profile of the optical interference pattern across the detector is measured by different elements of the detector and stored in an electronic processor (not shown) for analysis.

Interferometry system 100 includes a relay lens 236 configured so that the image of the part comes in focus on the detector. The input light from source 102 is imaged to pupil plane 114, and points on 124 are imaged to corresponding points on detector 134 (as indicated by marginal rays 116 and chief rays 117 from source 102).

Polarization elements 140, 142, 144, and 146 define the polarization state of the test and reference light being directed to the respective test and reference surfaces, and that of the combined light being directed to the detector. Depending on the embodiment, each polarization element can be a polarizer (e.g., a linear polarizer), a retardation plate (e.g., a half or quarter wave plate), or a similar optic that affects the polarization state of an incident beam. Furthermore, in some embodiments, one or more of the polarization elements can be absent. Moreover, depending on the embodiment, beam splitter 112 can be polarizing beam splitter or a non-polarizing beam splitter. Details of various embodiments for these polarization elements are described further below. In general, because of the presence of polarization elements 140, 142 and/or 146, the state of polarization of test light 122 at test surface 124 can be a function of the azimuthal position of the light in pupil plane 114.

In the presently described embodiment, source 102 provides illumination over a broad band of wavelengths (e.g., an emission spectrum having a full-width, half-maximum of more than 50 nm, or preferably, even more than 100 nm). For example, source 102 can be a white light emitting diode (LED), a filament of a halogen bulb, an arc lamp such as a Xenon arc lamp or a so-called supercontinuum source that uses non-linear effects in optical materials to generate very broad source spectra (>200 nm). The broad band of wavelengths corresponds to a limited coherence length. As in conventional scanning interferometer, a translation stage 150 adjusts the relative optic path length between the test and reference light to produce an optical interference signal at each of the detector elements. For example, in the embodiment of the FIG. 1, translation stage 150 is a piezoelectric transducer coupled to interference objective 106 to adjust the distance between the test surface and the interference objective, and thereby vary the relative optical path length between the test and reference light at the detector.

The interference signal measured at each detector element is analyzed by the electronic processor, which is electronically coupled to both detector 134 and translation stage 150. The electronic processor can transform the interference signal into the frequency domain, for example, by using a Fourier transform, to extract the phase and amplitude information about reflected wavefront from test surface 124.

Figure 2:
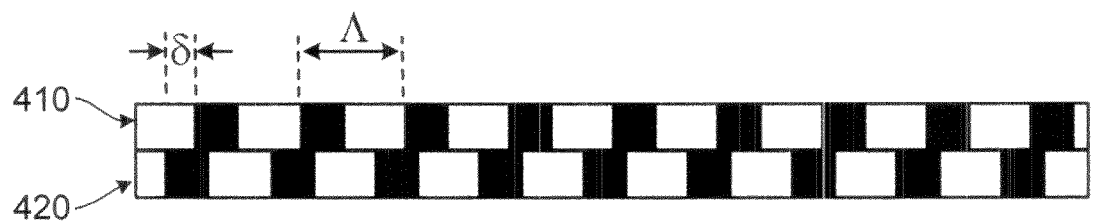
FIG. 2 is a schematic diagram of an overlay target in cross-section where one target layer is misregistered with respect to the other.

Referring to FIG. 2, the test object includes a pair of overlay target layers 410, 420 stacked on top of each other. In general, a variety of target geometries can be used but in the present embodiment each target pattern includes a periodic structure, both having period $\Lambda$. In general, $\Lambda$ will be in a range from $0.1\lambda$ to about $2\lambda$ (e.g., from $0.5\lambda$ to $1.5\lambda$, such as about $\lambda$), where $\lambda$ is the peak wavelength of the interferometry system light source. $\Lambda$ can be in a range from about 20 nm to about 1,000 nm (e.g., about 50 nm or more, about 100 nm or more, about 200 nm or more, about 400 nm or more, about 800 nm or less, about 600 nm or less). The target patterns can be formed from materials such as photoresists, dielectric materials, metals and/or semiconductors. Overlay target pattern 410 can be made of the same or different materials as overlay target pattern 420. During operation, interferometry system 100 is used to determine the relative position of the periodic structures between overlay target patterns 410 and 420, indicated by offset $\delta$. As shown in FIG. 2, the overlay target patterns are nominally symmetric, meaning, e.g., that if they are inverted about a vertical line through the center of FIG. 2, they have the same cross-sectional appearance.

Figures 3A, 3B:
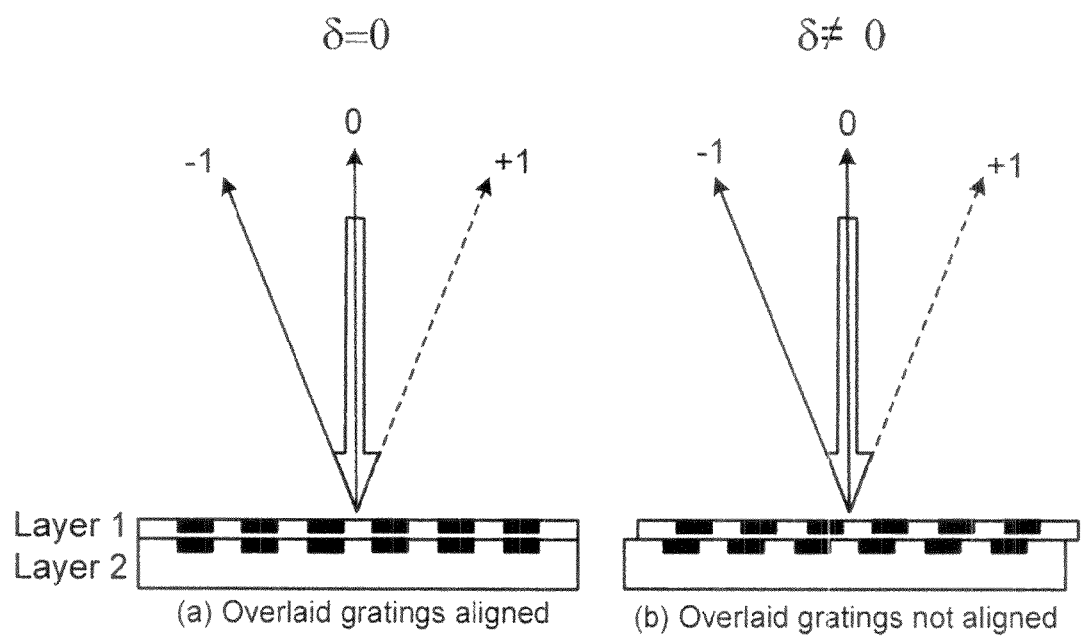
FIG. 3 is an illustration of diffraction of incident light from a grating target where the target structures are (a) registered and (b) offset with respect to each other.

Interferometry system 100 is set up to generate signals representative of the 3D reflected intensity and phase profile of the object. In the case where the grating targets of the two layers are perfectly aligned as in FIG. 3(a), i.e., $\delta=0$, the resulting 3D profile is symmetric. In the case of an offset between the grating targets of the two layers as in FIG. 3(b), i.e., $\delta\neq0$, the resulting 3D profile is asymmetric. This concept is discussed in more detail below in connection with FIGS. 4(a) and 4(b). Generally, the degree of asymmetry in the 3D profile is an indication of the misalignment of the grating targets corresponding to the overlaid layers.

Figure 4A:
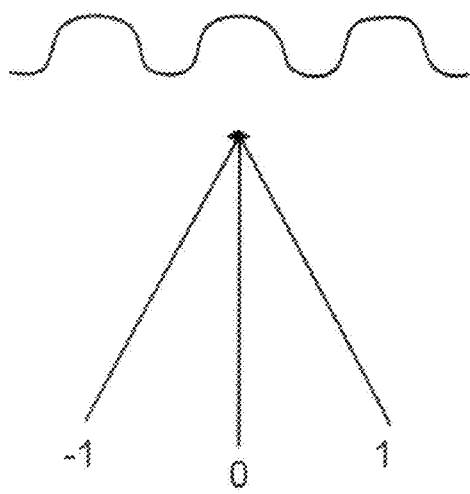
FIG. 4 is an illustration of phase imaging when there are three diffracted orders for target structures that are (a) registered and (b) offset with respect to each other.
Figure 4B:
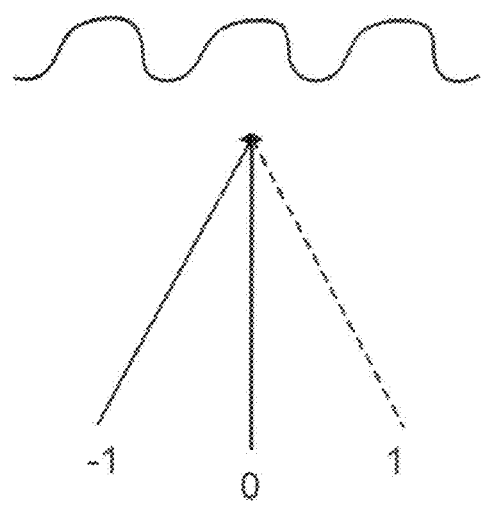

Without wishing to be bound by theory, the origin of the asymmetry may be understood qualitatively from the following example, based on the Abbé principle. Consider the case where the grating targets are of a fine pitch, so that the collection optics of the interferometric profiler capture three beams, $-1,0,+1$, illustrated in FIG. 3(a). On the imaging side, as shown in FIGS. 4(a) and 4(b), the three beams interfere. The phase of the $0^{th}$ order beam does not change spatially while the phases of the +1 and −1 beams change with opposite sign when moving laterally across the image. With balanced +1 and −1 beams (same amplitudes), moving to the one side is equivalent to moving to the other side because +1 and −1 beams just interchange their contributions to the field. The phase function becomes symmetric, as shown in FIG. 4(a). The symmetry is broken for the out-of-balance case where the complex amplitudes of the +1 and −1 beams are different. A corresponding phase function is shown in FIG. 4(b). The case of three diffracted beams described here is an example only—there are other grating structures and illumination conditions that may provide only two beams or more than three beams, but would nonetheless generate asymmetric results for offset grating targets between layers.

A more detailed analysis of the situation where there are three diffracted orders shows that the sum of fields arising from 0th, 1st and −1st order beams is $$E = 1 + a_2 e^{i(\phi_2 + k_x x)} + a_3 e^{i(\phi_3 - k_x x)}$$

where $k_x$ is the x-component of the wave vector of the first order diffracted beam in the camera plane (x is the spatial coordinate in the camera plane perpendicular to the images of the lines). For simplicity, the field has been scaled so that the zero order component becomes 1. The following substitution corresponds to a shift of the coordinate x. One sets $$x = \tilde{x} + (-\phi_2 + \phi_3)/2k_x$$

$$E = 1 + a_2 e^{i((\phi_2 + \phi_3)/2 + k_x \tilde{x})} + a_3 e^{i((\phi_2 + \phi_3)/2 - k_x \tilde{x})}$$

A further substitution $$\tilde{\phi} = (\phi_2 + \phi_3)/2$$

leads to $$E = 1 + a_2 e^{i(\tilde{\phi} + k_x \tilde{x})} + a_3 e^{i(\tilde{\phi} - k_x \tilde{x})}$$
$$= 1 + e^{i\tilde{\phi}} \cdot ((a_2 + a_3) \cdot \cos(k_x \tilde{x}) + i \cdot (a_2 - a_3)\sin(k_x \tilde{x}))$$

Interferometry allows one to measure field amplitude and angle as a function of the variable $\tilde{x}$. There are a variety of combinations of $a_2$, $a_3$, $\phi_2$ and $\phi_3$ that lead to different symmetries. A general case with $a_2 \neq a_3$ and $\tilde{\phi} \neq 0$ is shown in FIG. 5(a) showing the field in the complex plane.

The field vector follows an ellipse as the control variable $\tilde{x}$ increases. The figure also shows the minimum and maximum phase of the field $\Phi_{max}$ and $\Phi_{min}$. It becomes clear that it takes a smaller increase in $\tilde{x}$ to get from $\Phi_{max}$ to $\Phi_{min}$ than it takes to get from $\Phi_{min}$ back to $\Phi_{max}$. This results in an asymmetric phase $\Phi(\tilde{x})$, which is shown in FIG. 5(b).

Figure 5A:
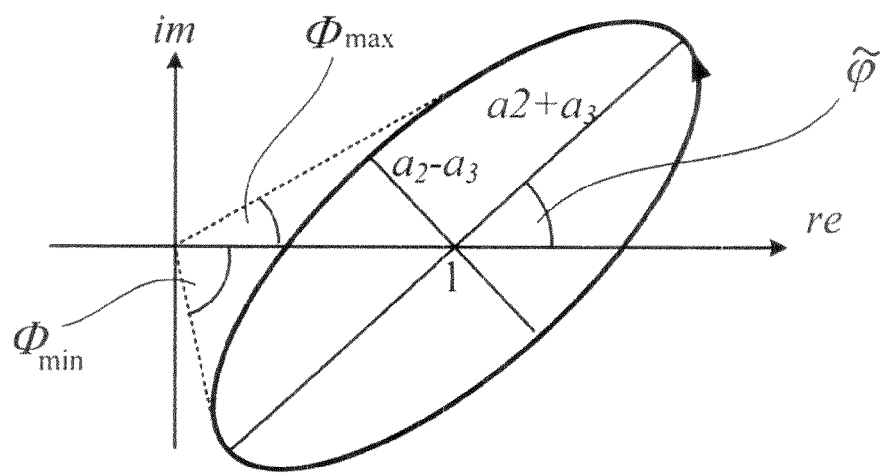
FIG. 5(a) is a schematic diagram showing an electric field resulting from interference of $-1^{st}$, $0^{th}$ and $1^{st}$ order.
Figure 5B:
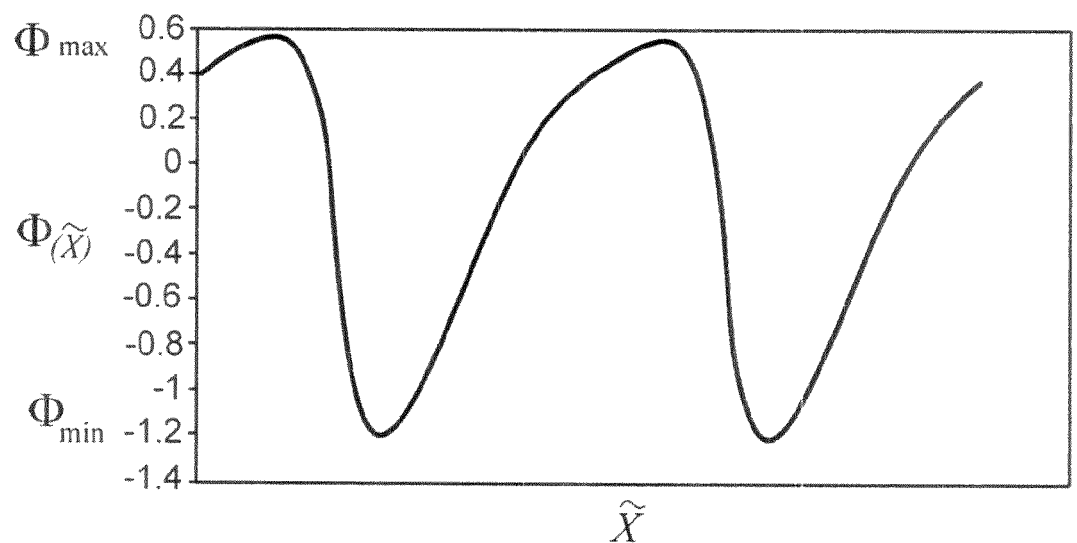
FIG. 5(b) is a plot showing a phase of the field resulting from the interference of $-1^{st}$, $0^{st}$ and $1^{st}$ order beams, shown as a function of the spatial variable $\tilde{x}$.

From FIG. 5(a) it is apparent that for the special condition $a_2 = a_3$ and $\tilde{\phi} = 0$ the resulting phase is constant. The conditions $a_2 = a_3$ and $\tilde{\phi} \neq 0$ lead to a symmetric $\Phi(\tilde{x})$. If any of the last two cases happens to occur for one specific wavelength, at least one other wavelength in the white light spectrum will most likely result in an asymmetry. Similar asymmetry arguments hold for the amplitude or intensity. The points on the ellipse closest and furthest from the origin correspond to the minimum and maximum of the intensity function $I(\tilde{x}) \propto E^2$. Again, it takes a smaller increase in $\tilde{x}$ to get from $I_{max}$ to $I_{min}$ than it takes to get from $I_{min}$ back to $I_{max}$.

Figure 13A:
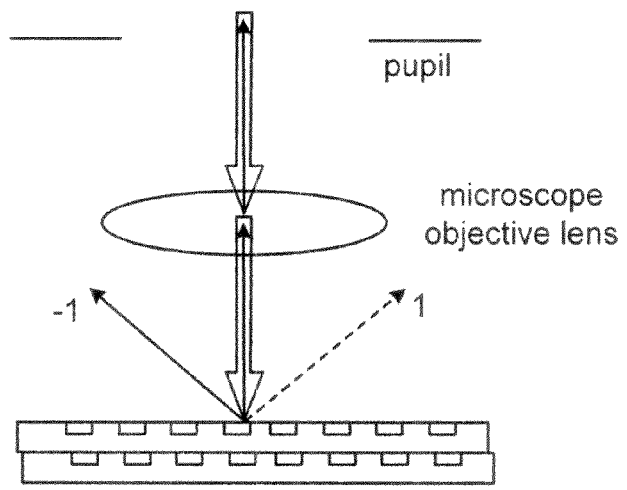
FIGS. 13(a)-13(c) are schematic diagrams showing the relationship between diffracted orders and the geometry of a microscope objective.
Figures 13B, 13C:
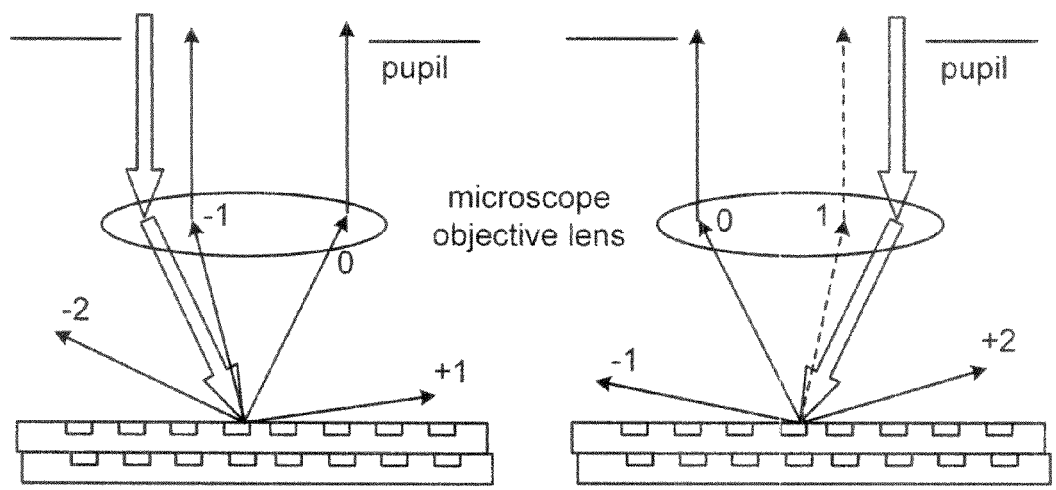

The case of three diffracted beams described here is an example only—there are other grating structures and illumination conditions that may provide only two beams or more than three beams, but would nonetheless generate asymmetric measurements in the presence of target layer offsets. For example, by decreasing the grating period or choosing a longer illumination wavelength, the angular separation of the diffraction orders becomes larger, possibly too large to be captured by the microscope objective. FIG. 13(a) shows such a situation where only the $0^{th}$ order reflected beam of an on-axis illumination beam is captured by the objective. In FIGS. 13(b) and 13(c) two mutually symmetric illumination beams are shown, which illuminate the same sample at an angle, allowing the 1st or −1st diffraction order to be captured by the microscope objective. All of the captured beams in FIGS. 13(b) and 13(c) contribute to the interference scan which becomes asymmetric if the −1st diffraction order in FIG. 13(b) and the 1st diffraction order in FIG. 13(c) differ due to the presence of an overlay offset.

If we define A as the pitch of the periodic overlay structure, λ the wavelength of the light used for the measurement and NA the numerical aperture of the microscope objective, the condition $\lambda/2NA < \Lambda < \lambda/NA$ defines the range of pitches for which only two diffraction orders (0th and one of +1 or −1) are captured by the optics, as in FIGS. 13(b) and 13(c). This situation is relevant for typical microscope configurations using visible light.

Figures 6A, 6B:
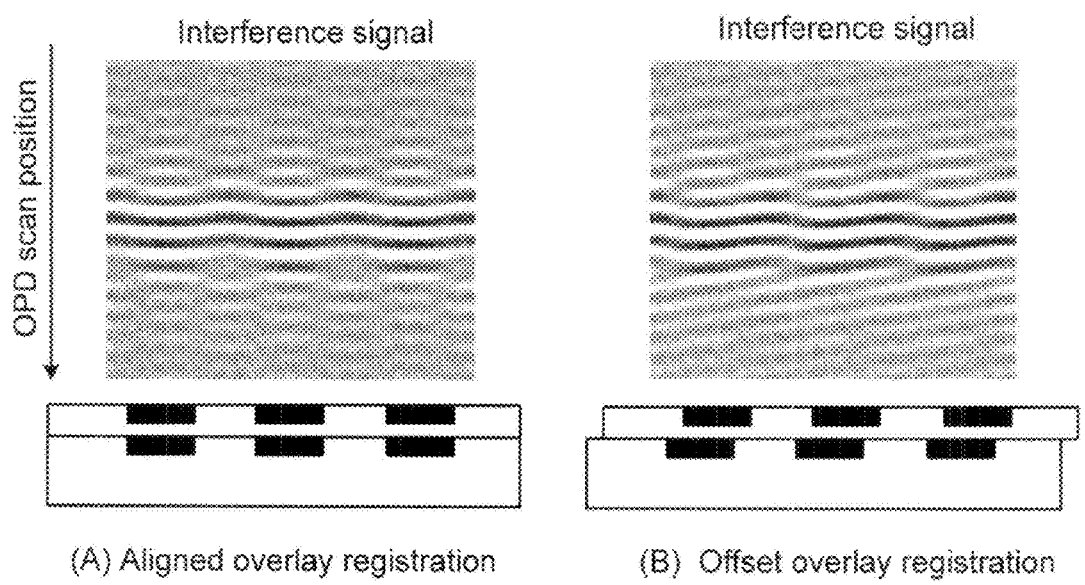
FIG. 6 shows an illustration of (a) symmetric and (b) asymmetric interference signals for a scanning white light interferometer viewing aligned and offset target layers, respectively.

Data from a simulated OPD scan is shown in FIGS. 6(a) and 6(b). These figures show a cross-section of the interference intensity stored as function of scan position (vertical axis) for the case of grating targets that are aligned (FIG. 6(a)) and offset (FIG. 6(b)) with respect to each other as shown in the figure. The horizontal axis in the plots represents a lateral dimension of the imaging sensor orthogonal to the image of the grating lines, i.e., columns in the plots correspond to camera pixels. The interference intensity signal is in this case for a scanning white-light interferometer with Köhler illumination, and an imaging aperture that accepts at most a zero and a single first-order diffracted beam for every illumination point in the pupil. The simulation assumes a spectrally-broadband illumination centered at a wavelength of 450 nm, and a 0.78NA objective and a target-grating pitch of 500 nm.

Figure 7A:
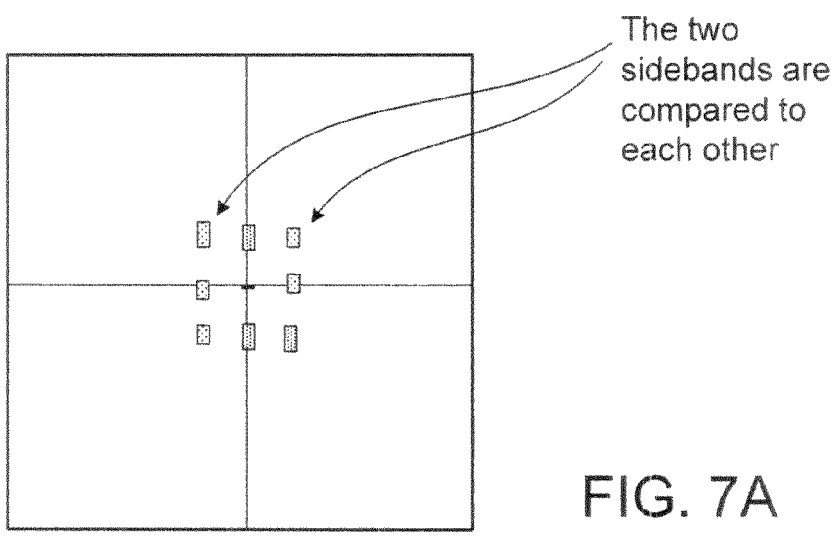
FIG. 7(a) is a plot of a 2D Fourier transform of the signal shown in FIG. 6(b). Differences in the two sidebands reveal asymmetries in the original signal.
Figure 7B:
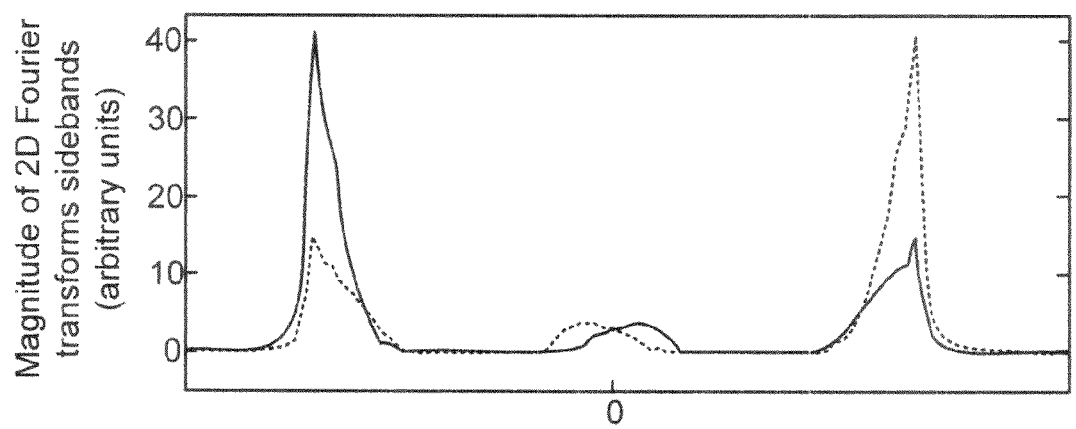
FIG. 7(b) is a detail plot of the two sidebands of the 2D Fourier transform signal shown in FIG. 6(b) (dotted: left sideband; solid: right sideband).

For the example data shown in FIGS. 6(a) and 6(b), an effective signal processing technique that can be used is to perform a 2D Fourier transform of the interference signal vs. OPD scan position cross section. The 2D transform readily reveals asymmetries in the signal, indicative of an overlay offset between the registration target patterns. FIG. 7(a) shows the magnitude of the 2D-Fourier transform of the asymmetric interference signal shown in FIG. 6(b). There are 3 bands that carry information about the signal. The central band can be interpreted as the 1D Fourier transform of the signal averaged over all camera pixels. The signal asymmetry, however, is captured in the two side bands. Those side bands represent the change of single pixel signal 1D Fourier transforms as you move across pixels. FIG. 7(b) shows a side-by-side plot of those two side bands.

The difference between these two curves is clear in this example, where the overlay shift was chosen to be as big as 100 nm with a 500 nm pitch structure (i.e., as big as 0.2Λ). In general, overlay shifts and therefore also the asymmetries can be much smaller (e.g., 0.1Λ or less, 0.05Λ or less, 0.01Λ or less). For very small overlay shifts, the difference between the two sidebands maps close to linear to the overlay shift. In the evaluation procedure either single Fourier components, a group of Fourier components or all the information in those sidebands can be used. Larger pitch structures or the use of shorter wavelength light can lead to more than 2 sidebands in the 2D Fourier transform, all of which can be used for the analysis.

In certain embodiments, an optical profiler equipped with a 2-dimensional detector captures interference data that are redundant along lines of pixels that are parallel to the lines of the overlay gratings. By averaging the interference signal of such pixels, a computer can create a version of the data represented in FIGS. 7(a) and 7(b) that benefits from reduced electronic and optical noise.

In some embodiments, tilt of the overlay test pad with respect to the interferometer can be accommodated by processing the interference data to first generate a height map of the object surface, e.g., using conventional SWLI procedures. One can then determine the tilt of the surface by fitting a plane through the height data. This information is then used to correct for tilt in the following fashion: (1) Fourier transform the signal of each individual pixel of interest, (2) separate the magnitude and phase of the Fourier transform, (3) add a linear phase term to the spectral phase component to compensate the effect of the local object height and (4) calculate the inverse Fourier transform to generate a new interference signal free of height variations related to tilt. The corrected signals are then used to generate a data representation such as that shown in FIGS. 7(a) and 7(b).

In the case of a broadband light source and/or interferometer using a high-NA objective the interference signal at each pixel corresponds to a range of frequencies that can be separated by Fourier transformation. One can then select one or multiple frequency bands within the spectrum to create a new interference signal by subsequent inverse Fourier transformation. In this way it is possible to create multiple versions the data represented in FIGS. 7(a) and 7(b) for different source wavelengths and/or different illumination directions. The goal is to increase (e.g., maximize) the sensitivity of the method, for example by taking into account the optical properties of the materials used to create the overlay test structures.

Other signal processing techniques can be applied to extract asymmetry information from interference patterns, such as other transformation operations (e.g., Hermit, Laplace), cellular automata, wavelet methods, etc.

Figure 8A:
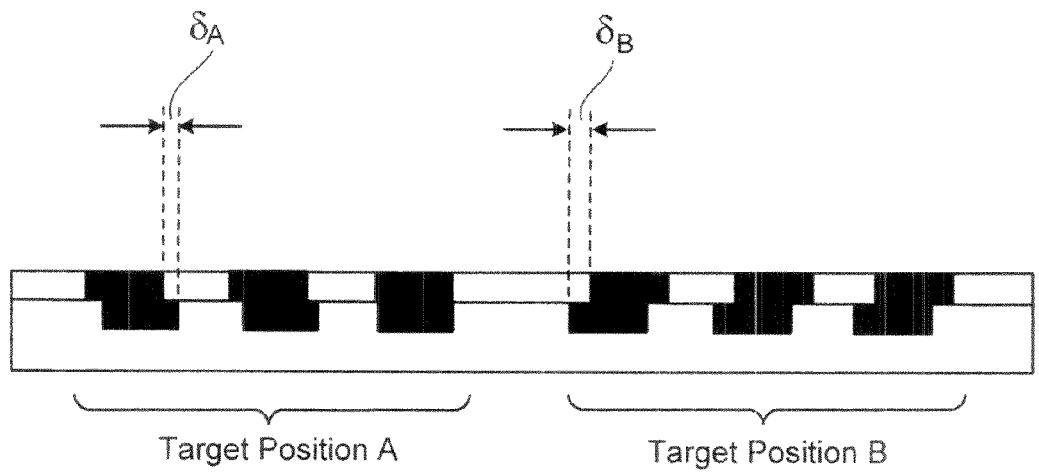
FIG. 8(a) is a schematic diagram of a target layout with fixed overlay registration offsets between target position A and target position B.

In general, overlay targets may be positioned on the object in a variety of ways to accurately measure overlay registration. For example, in some embodiments, a pair of target patterns are arranged with opposite fixed offsets, as in shown in FIG. 8(a). This layout facilitates a differential measurement, wherein the overlay registration is measured by detecting the difference in asymmetry between signals measured over target pattern A in comparison with target pattern B. A differential measurement can reduce requirements on the absolute accuracy of the optical modeling that quantitatively relates asymmetry to overlay registration errors.

Using a single overlay target pattern, optical modeling is typically required to derive the overlay registration by comparison of the measured signal asymmetry with the modeled signal asymmetry. For those embodiments that rely on a linear asymmetry change as a function of overlay (e.g. differential techniques with two targets), optical modeling can be used beforehand to verify that the tool has sufficient linearity over the operating range or, if there is nonlinearity, the simulated degree of nonlinearity may be used for a compensation procedure. Generally, accurate results of optical modeling require the knowledge of structure parameters, such as film thicknesses, grating line thicknesses, line heights, side wall angles material indices, etc. Those structure parameters may be known from previous process control metrology, potentially using the same instrument in a different configuration where the pupil of the interference objective is imaged (see, for example, the configuration described further below). Using more than two overlay target patterns with a series of fixed overlay offsets can relax the requirement for linearity in differential measurements. Modeling can also be useful in designing optimized target structures or in finding optimal instrument settings such as polarization or wavelength and angular ranges.

Because the interferometry system used is an imaging system, multiple targets may be measured simultaneously in a single field of view. In certain embodiments, two pairs of target patterns arranged orthogonally and simultaneously provide both x and y registration information.

Figure 8B:
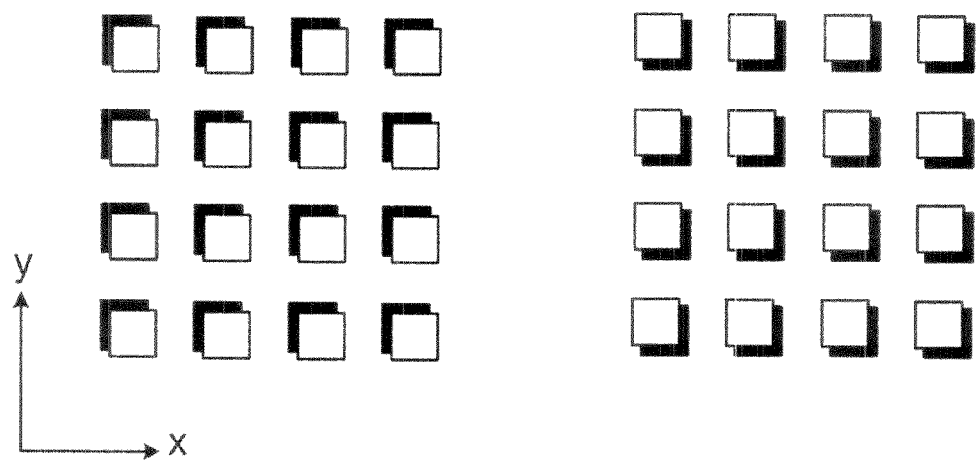
FIG. 8(b) is a schematic representation of two 2D overlay targets with opposite intentional offsets for the determination of overlay in two dimensions. The white squares represent the periodic structure in the top layer and the partially covered black features represent the periodic structure in a different layer.

In general, measuring overlay in two dimensions can be achieved in a variety of ways. For example, one approach is to double the number of targets, for example from two targets to four targets, where the first pair of targets with grating lines running in the y-direction is made for the determination of overlay in x and the second pair of targets with grating lines running in the x-direction is made for the determination of overlay in y. In some embodiments, however, patterns that are periodic in two dimensions are used, thereby reducing the number of required targets by a factor of two. FIG. 8(b) shows an example of two targets in which the patterns have opposite intentional offsets in x and in y. They can be used in differential measurements. The analysis of signal asymmetries is done in two dimensions. The previously described 2D Fourier transforms are replaced by 3D Fourier transforms resulting in $F(\omega_X, \omega_Y, \omega_Z)$, where $\omega_X$, for example, is the normalized frequency with the value 1 representing a signal period equivalent to the period (in x) of the image of the grating. Signal asymmetry in x indicative of overlay in x can be identified by comparing $F(1, 0, \omega_Z)$ against $F(-1, 0, \omega_Z)$ and signal asymmetry in y indicative of overlay in y can be identified by comparing $F(0, 1, \omega_Z)$ against $F(0, -1, \omega_Z)$, for instance.

In certain embodiments, multiple measurements with differently polarized light may be taken on each target in order to maximize signal sensitivity to overlay in the x and the y direction. Microscope configurations with a linear polarizer in the illumination path oriented in the x or y direction and an analyzer in the imaging path oriented in the x or y direction can be used, for example, in order to minimize cross-talk between x overlay and y signal asymmetries and vice versa.

While a particular interferometry system is shown in FIG. 1, in general, the methods can be implemented using with a wide variety of optical interferometric systems that provide at least 2D interference phase (i.e., linear measurements from left to right across the target cross sections shown in FIG. 2). For example, while the light source described for interferometry system 100 is a broadband light source, in general, interferometry systems used for overlay measurements may use monochromatic or broadband light sources. Further, the light source can be a spatially extended light source, e.g., filling the pupil of the objective (e.g., Köhler illumination); but a single source point (e.g., critical illumination) is also feasible.

Furthermore, interferometry systems used for overlay measurements can, in embodiments, be used for other types of metrology as well. For example, interferometry system 100 can be used for surface profiling in addition to overlay measurements. Alternatively, or additionally, interferometry systems can also be adapted for additional functionality by switching between various hardware configurations.

Figure 9:
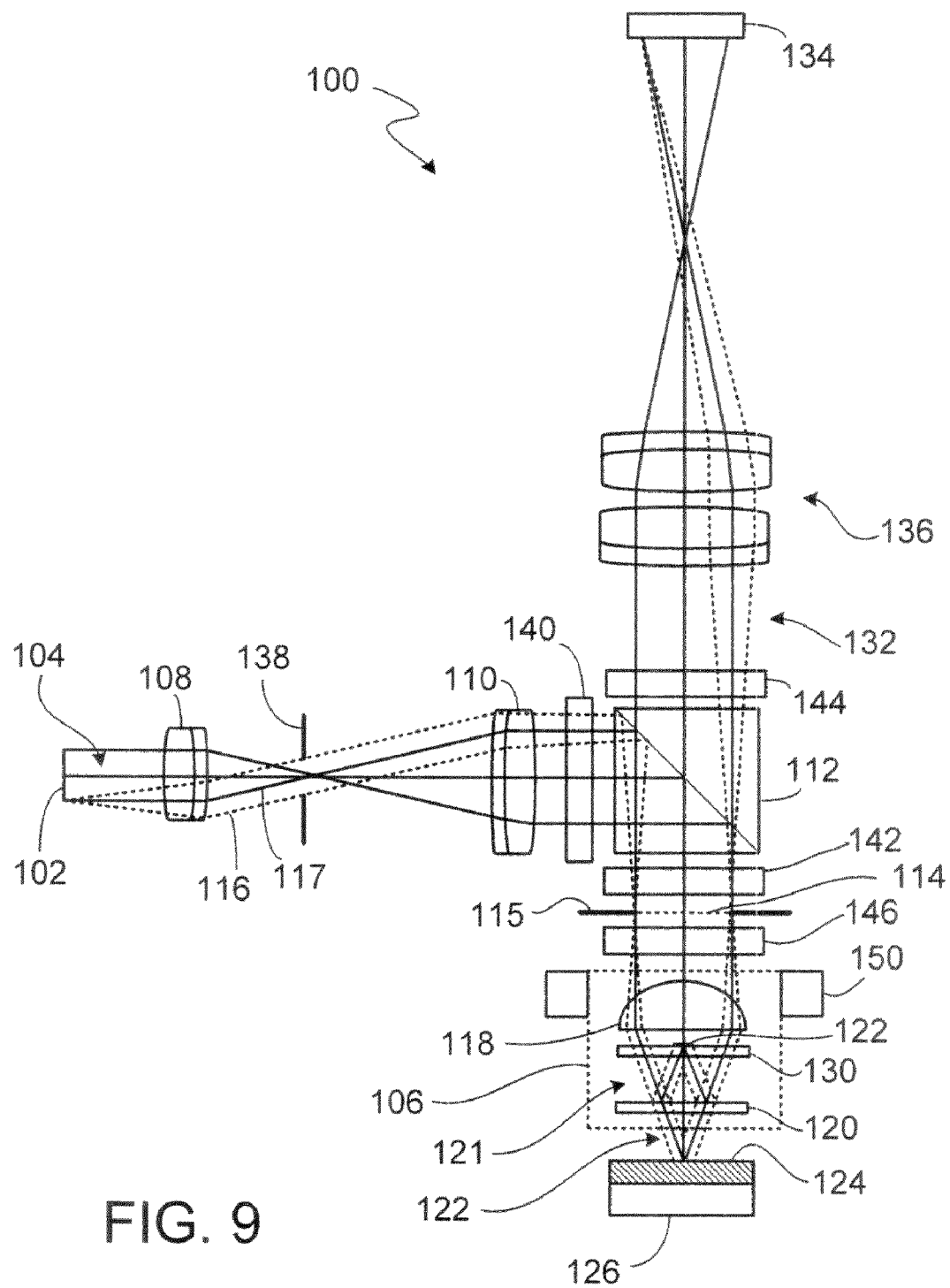
FIG. 9 is a schematic diagram of interferometry system 100 reconfigured to operate in an ellipsometry mode.

For example, referring to FIG. 9, in certain embodiments, unlike a conventional profiling interferometer as shown in FIG. 1, in which the test surface is imaged onto the detector, relay lens 236 can be switched out for a different relay lens 136 (e.g., a Bertrand lens), which images different points on the pupil plane 114 to corresponding points on detector 134 (again as illustrating by dotted marginal rays 116 and solid chief rays 117).

Because each source point illuminating pupil plane 114 creates a plane wave front for test light 121 illuminating test surface 124, the radial location of the source point in pupil plane 114 defines the angle of incidence of this illumination bundle with respect to the object normal. Thus, all source points located at a given distance from the optical axis correspond to a fixed angle of incidence, by which objective lens 118 focuses test light 122 to test surface 124. A field stop 138 positioned between relay optic 108 and 110 defines the area of test surface 124 illuminated by test light 122. After reflection from the test and reference surfaces, combined light 132 forms a secondary image of the source at pupil plane 114 of the objective lens. Because the combined light on the pupil plane is then re-imaged by relay lens 136 onto detector 134, the different elements of the detector 134 correspond to the different illumination angles of test light 122 on test surface 124.

Because of the arrangement of interferometry system 100 as shown in FIG. 9, each detector element of electronic detector 134 provides reflectivity measurements at a multiplicity of wavelengths produced by source 102, for a specific angle of incidence and polarization state (according to the orientations of polarization elements 140, 142, 144 and/or 146). The collection of detector elements thus covers a range of angles of incidence, polarization states and wavelengths, which maximizes the ability of the instrument to properly characterize unknown optical structures.

Additional discussion of the theory of operation and calibration of interferometry system 100, as depicted in both FIG. 1 and FIG. 9, can be found in US-2006-015659-A1, the entire contents of which is incorporated herein by reference.

Figure 10:
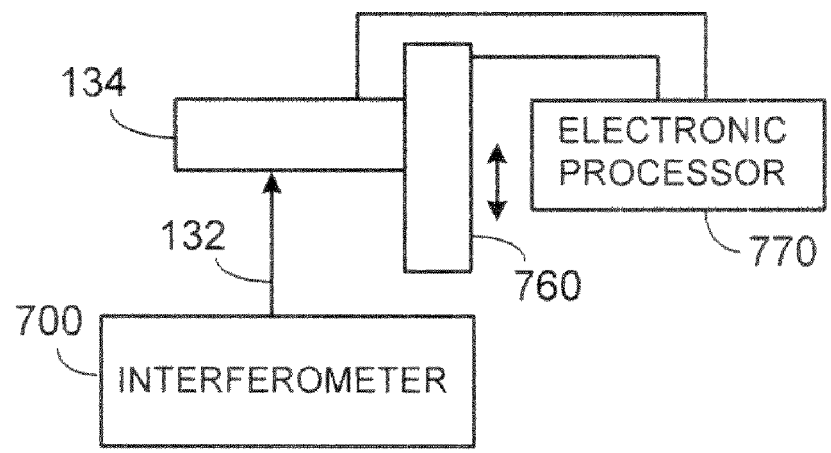
FIG. 10 is a schematic diagram of another embodiment for interferometry system 100.

Instead of switching between relay lens 236 and 136, in further embodiments, for example, the relay lens can be left alone and detector 134 can be translated to a position where the test surface is in focus. This is shown schematically in FIG. 10, which shows detector 134 coupled to a motorized translation stage 760 under the control of electronic processor 770 to adjust the detector position for receiving combined light 132 relative to the rest of the interferometry system 700. The translation stage allows the system to switch between a first position corresponding the ellipsometry mode, in which the pupil plane is imaged to the detector, and a second position corresponding to the profiling/overlay mode, in which the test surface is imaged to the detector and overlay and/or surface profiling can be monitored.

Figure 11:
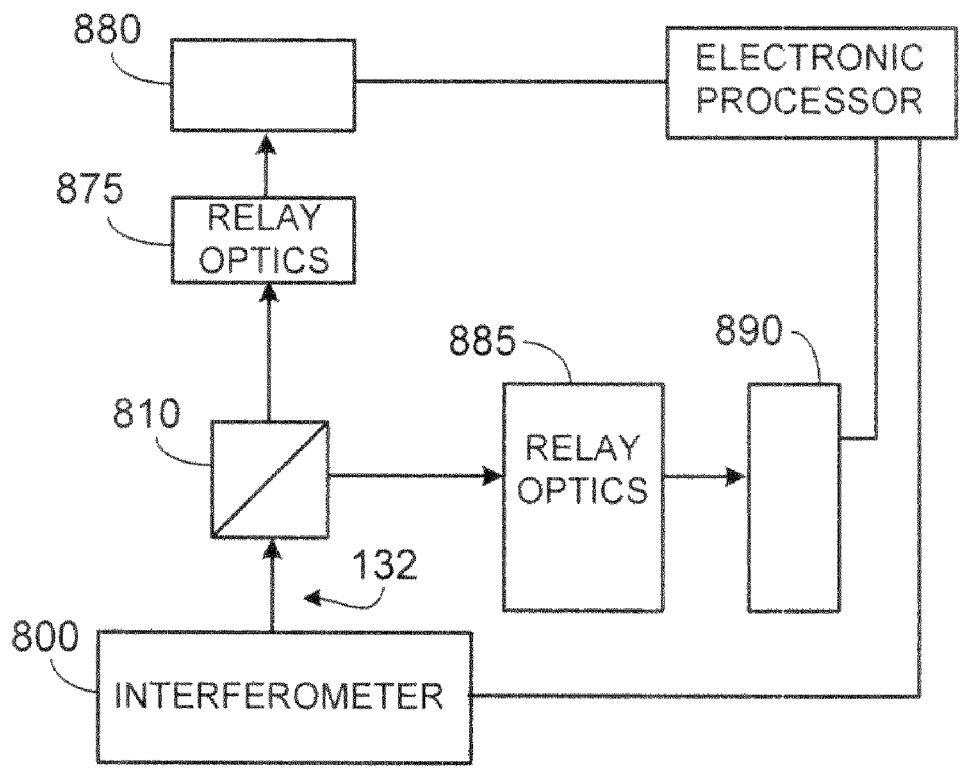
FIG. 11 is a schematic diagram of yet another embodiment for interferometry system 100.

In yet a further embodiment, shown schematically in FIG. 11, a beam splitter 810 can split the combined light 132 received from the rest of the interferometry system 800 into two channels with two corresponding multi-element detectors 880 and 890, with one channel using relay optics 875 to image pupil plane 114 to the first detector 880 to provide the ellipsometry mode measurement and the other channel using relay optics 885 to image the test surface to the second detector 890 to simultaneously provide the profiling mode measurement. Both detectors are coupled to electronic processor 870, which analyze the detector images as described above.

Various combinations of these approaches are also possible. For example, the system can include optics that image the pupil plane to a first portion of a common electronic detector and image the test surface to a second portion of the common electronic detector. In this case, the different portions of the common electronic detector can be considered to be separate detectors.

Figure 12:
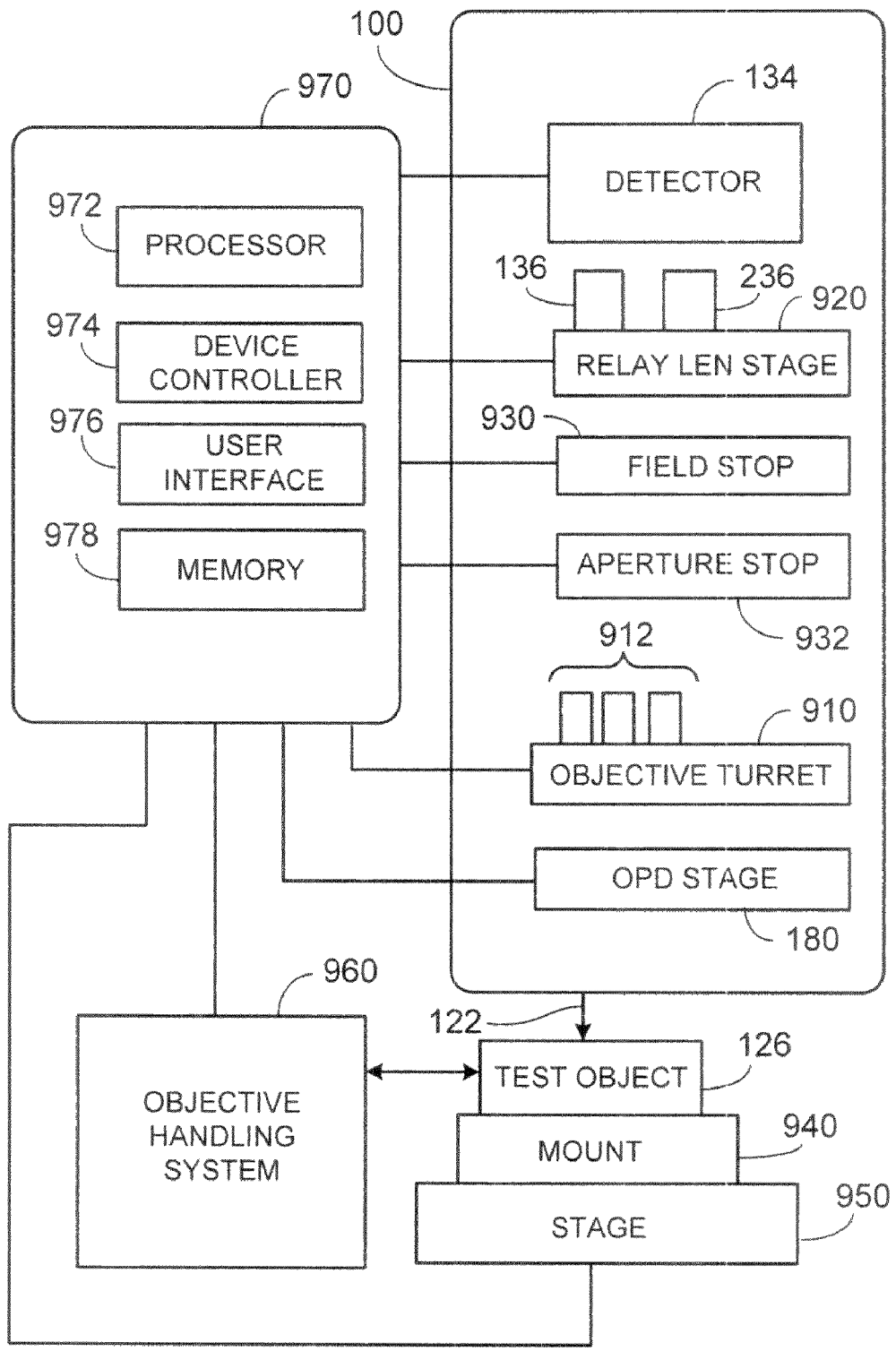
FIG. 12 is a schematic diagram of interferometry system 100 showing how various components can be adjusted in an automated fashion under the control of an electronic processor.

FIG. 12 shows a schematic diagram of how various components in interferometry system 100 can be automated under the control of electronic processor 970, which, in the presently described embodiment, can include an analytical processor 972 for carrying out mathematical analyses, device controllers 974 for controlling various components in the interferometry system, a user interface 976 (e.g., a keyboard and display), and a storage medium 978 for storing calibration information, data files, a sample models, and/or automated protocols.

First, the system can include a motorized turret 910 supporting multiple objectives 912 and configured to introduce a selected objective into the path of input light 104. One or more of the objectives can be interference objectives, with the different interference objectives providing different magnifications. Furthermore, in certain embodiments, one (or more) of the interference objectives can be especially configured for the ellipsometry mode of operation by having polarization element 146 (e.g., a linear polarizer) attached to it. The remaining interference objectives can be used in the profiling mode and, in certain embodiments, can omit polarization element 146 so as to increase light efficiency (such as for the embodiment described above in which beam splitter 112 is a polarizing beam splitter and polarization element is 142 is a quarter wave plate). Moreover, one or more of the objectives can be a non-interferometric objective (i.e., one without a reference leg), each with a different magnification, so that system 100 can also operate in a conventional microscope mode for collecting optical images of the test surface (in which case the relay lens is set to image of test surface to the detector). Turret 910 is under the control of electronic processor 970, which selects the desired objective according to user input or some automated protocol.

Next, the system includes a motorized stage 920 (e.g., a tube lens holder) for supporting relay lenses 136 and 236 and selectively positioning one of them in the path of combined light 132 for selecting between the first mode (e.g., an ellipsometry or reflectometry mode) in which the pupil plane 114 is imaged to the detector and the second mode (e.g., profiling/overlay or microscope mode) in which the test surface is imaged to the detector. Motorized stage 920 is under the control of electronic processor 970, which selects the desired relay lens according to user input or some automated protocol. In other embodiments, in which a translation stage is moved to adjust the position of the detector to switch between the first and second modes, the translation is under control of electronic processor. Furthermore, in those embodiments with two detection channels, each detector is coupled to the electronic processor 970 for analysis.

Furthermore, the system can include motorized apertures 930 and 932 under control of electronic processor 970 to control the dimensions of field stop 138 and aperture stop 115, respectively. Again the motorized apertures are under the control of electronic processor 970, which selects the desired settings according to user input or some automated protocol.

Also, translation stage 150, which is used to vary the relative optical path length between the test and reference legs of the interferometer, is under the control electronic processor 970. As described above, the translation stage can be coupled to adjust the position of the interference objective relative to a mount 940 for supporting test object 126. Alternatively, in further embodiments, the translation stage can adjust the position of the interferometry system as a whole relative to the mount, or the translation stage can be coupled to the mount, so it is the mount that moves to vary the optical path length difference.

Furthermore, a lateral translation stage 950, also under the control of electronic processor 970, can be coupled to the mount 940 supporting the test object to translate laterally the region of the test surface under optical inspection. In certain embodiments, translation stage 950 can also orient mount 940 (e.g., provide tip and tilt) so as to align the test surface normal to the optical axis of the interference objective.

Finally, an object handling station 960, also under control of electronic processor 970, can be coupled to mount 940 to provide automated introduction and removal of test samples into system 100 for measurement. For example, automated wafer handling systems known in the art can be used for this purpose. Furthermore, if necessary, system 100 and object handling system can be housed under vacuum or clean room conditions to minimize contamination of the test objects.

The resulting system provides great flexibility for providing various measurement modalities and procedures. For example, the system can first be configured in the microscope mode with one or more selected magnifications to obtain optical images of the test object for various lateral positions of the object. Such images can be analyzed by a user or by electronic processor 970 (using machine vision techniques) to identify certain regions (e.g., specific structures or features, landmarks, fiducial markers, defects, etc.) in the object. Based on such identification, selected regions of the sample can then be studied in the ellipsometry mode to determine sample properties (e.g., refractive index, underlying film thickness(es), material identification, etc.).

Accordingly, the electronic processor causes stage 920 to switch the relay lens to the one configured for the ellipsometry mode and further causes turret 910 to introduce a suitable interference objective into the path of the input light. To improve the accuracy of the ellipsometry measurement, the electronic processor can reduce the size of the field stop via motorized aperture 930 to isolate a small laterally homogenous region of the object. After the ellipsometry characterization is complete, electronic processor 970 can switch the instrument to the profiling mode, selecting an interference objective with a suitable magnification and adjusting the size of field stop accordingly. As described above, the profiling/overlay mode captures interference signals that allow reconstructing the topography of, for example, one or more interfaces that constitute the object. Notably, as described in greater detail below, the knowledge of the optical characteristics of the various materials determined in the ellipsometry mode allows for correcting the calculated topography for thin film or dissimilar material effects that would otherwise distort the profile. See, for example, U.S. patent application Ser. No. 10/795,579 entitled "PROFILING COMPLEX SURFACE STRUCTURES USING SCANNING INTERFEROMETRY" and published as U.S. Patent Publication No. US-2004-0189999-A1, which was incorporated by reference above. If desired, the electronic processor can also adjust the aperture stop diameter via motorized aperture 932 to improve the measurement in any of the various modes.

When used in conjunction with automated object handling system 960, the measurement procedure can be repeated automatically for a series of samples. This could be useful for various process control schemes, such as for monitoring, testing, and/or optimizing one or more semiconductor processing steps.

For example, the system can be used in a semiconductor process for tool specific monitoring or for controlling the process flow itself. In the process monitoring application, single/multi-layer films are grown, deposited, polished, or etched away on unpatterned Si wafers (monitor wafers) by the corresponding process tool and subsequently the thickness and/or optical properties are measured using the interferometry system disclosed herein (for example, by using the ellipsometry mode, the profiling/overlay mode, or both). The average, as well as within wafer uniformity, of thickness (and/or optical properties) of these monitor wafers are used to determine whether the associated process tool is operating with targeted specification or should be retargeted, adjusted, or taken out of production use.

In the process control application, latter single/multi-layer films are grown, deposited, polished, or etched away on patterned Si, production wafers by the corresponding process tool and subsequently the thickness and/or optical properties are measured with the interferometry system disclosed herein (for example, by using the ellipsometry mode, the profiling mode, or both). Production measurements used for process control typical include a small measurement site and the ability to align the measurement tool to the sample region of interest. This site may consists of multi-layer film stack (that may itself be patterned) and thus requires complex mathematical modeling in order to extract the relevant physical parameters. Process control measurements determine the stability of the integrated process flow and determine whether the integrated processing should continue, be retargeted, redirected to other equipment, or shut down entirely.

Specifically, for example, the interferometry system disclosed herein can be used to monitor the following equipment: diffusion, rapid thermal anneal, chemical vapor deposition tools (both low pressure and high pressure), dielectric etch, chemical mechanical polishers, plasma deposition, plasma etch, lithography track, and lithography exposure tools. Additionally, the interferometry system disclosed herein can be used to control the following processes: trench and isolation, transistor formation, as well as interlayer dielectric formation (such as dual damascene).

In some embodiments, light source 102 in system 100 of FIG. 1 is replaced by a tunable monochromatic source under the control of the electronic processor. For example, the source can be a tunable laser diode or a broadband source incorporating a tunable spectral filter to produce a tunable spectral output (e.g., a monochromator, a spectral filter wheel, or a tunable liquid crystal filter.) Furthermore, the position of reference mirror 122 is adjusted so that the optical path length difference between the test light and reference light when the test surface is in-focus with respect to the interference objective is non-zero. Detector 134 records the interference pattern produced by the combined light as the wavelength of the source is scanned. There is no mechanical motion of the object with respect to the interferometric objective in this case. Because of the adjustment in the position of the reference mirror and the resulting non-zero optical path length difference between the test and reference legs of the interferometer, the scanning of the source frequency produces an interference signal that is measured at each detector element. This interference signal is sometimes referred to as a "channel spectrum."

When operating in the ellipsometry mode (e.g., as in FIG. 9), the intensity of the interference signal measured at each detector element follows from the equations for the sum of fields, E, presented above, except that "z" is fixed at the non-zero optical path length difference, and the wavenumber k is varied. During analysis, the electronic processor determines the wavelength-dependent, complex reflectivity of the test surface from the interference cross-term in E using a analytical framework similar to that shown above. For example, the interference signal at each detector element can be Fourier transformed, filtered to select the portion of the transformed signal corresponding to the cross-term, and then inversed Fourier transformed to give the magnitude and phase of the signal with respect to wavelength. This magnitude and phase can then be related as to ellipsometry parameters in a similar fashion to that described above. When operating in the profiling mode (as in FIG. 3), the interference signal in the present embodiment can be Fourier transformed, and variations in the phase at the non-zero optical path length difference coordinate in the transform over the various detector elements can be related changes in the topography of the test surface. Information from the other coordinates in the Fourier transform can also be analyzed to provide topography information.

Accordingly, this narrow-band, tunable source embodiment can also operate in the various modes of operation and for the various applications described above.

The embodiments shown in FIGS. 1 and 9 use an interference objective of the Mirau-type, in which the beam splitter in the interference objective directs the reference light back along the optical axis for the test light. In other embodiments, interferometry system 100 can instead use a different type of interference objective, such as a Michelson objective, in which the beam splitter directs the reference light away from the optical axis of the test light (e.g., the beam splitter can be oriented at 45 degrees to the input light so the test light and reference travel at right angles to one another). In such cases, the reference surface can be positioned outside of the path of the test light.

In another embodiment, the interference objective can be of the Linnik-type, in which the case the beam splitter is positioned prior to the objective lens for the test surface (with respect to the input light) and directs the test and reference light along different paths. A separate objective lens is used to focus the reference light to the reference lens. In other words, the beam splitter separates the input light into the test and reference light, and separate objective lenses then focus the test and reference light to respective test and reference surfaces. Ideally the two objective lenses are matched to one another so that the test and reference light have similar aberrations and optical paths.

Additional interferometer configurations are also possible. For example, the system can be configured to collect test light that is transmitted through the test sample and then subsequently combined with reference light. For such embodiments, for example, the system can implement a Mach-Zehnder interferometer with dual microscope objectives on each leg.

The light source in the interferometer may be any of: an incandescent source, such as a halogen bulb or metal halide lamp, with or without spectral bandpass filters; a broadband laser diode; a light-emitting diode; a supercontinuum light source (as mentioned above); a combination of several light sources of the same or different types; an arc lamp; any source in the visible spectral region; any source in the IR spectral region, particularly for viewing rough surfaces & applying phase profiling; and any source in the UV spectral region, particularly for enhanced lateral resolution. For broadband applications, the source preferably has a net spectral bandwidth broader than 5% of the mean wavelength, or more preferably greater than 10%, 20%, 30%, or even 50% of the mean wavelength. For tunable, narrow-band applications, the tuning range is preferably broad (e.g., greater than 50 nm, greater than 100 nm, or greater than even 200 nm, for visible light) to provide reflectivity information over a wide range of wavelengths, whereas the spectral width at any particular setting is preferable narrow, to optimize resolution, for example, as small as 10 nm, 2 nm, or 1 nm. The source may also include one or more diffuser elements to increase the spatial extent of the input light being emitted from the source.

Furthermore, the various translations stages in the system, such as translation stage 150, may be: driven by any of a piezo-electric device, a stepper motor, and a voice coil; implemented opto-mechanically or opto-electronically rather than by pure translation (e.g., by using any of liquid crystals, electro-optic effects, strained fibers, and rotating waveplates) to introduce an optical path length variation; any of a driver with a flexure mount and any driver with a mechanical stage, e.g. roller bearings or air bearings.

The electronic detector can be any type of detector for measuring an optical interference pattern with spatial resolution, such as a multi-element CCD or CMOS detector.

The analysis steps described above can be implemented in computer programs using standard programming techniques. Such programs are designed to execute on programmable computers or specifically designed integrated circuits, each comprising an electronic processor, a data storage system (including memory and/or storage elements), at least one input device, and least one output device, such as a display or printer. The program code is applied to input data (e.g., images from the detector) to perform the functions described herein and generate output information (e.g., overlay error, refractive index information, thickness measurement(s), surface profile(s), etc.), which is applied to one or more output devices. Each such computer program can be implemented in a high-level procedural or object-oriented programming language, or an assembly or machine language. Furthermore, the language can be a compiled, interpreted or intermediate language. Each such computer program can be stored on a computer readable storage medium (e.g., CD ROM or magnetic diskette) that when read by a computer can cause the processor in the computer to perform the analysis and control functions described herein.

Interferometry metrology systems, such as those discussed previously, can be used in the production of integrated circuits to monitor and improve overlay between patterned layers. For example, the interferometry systems and methods can be used in combination with a lithography system and other processing equipment used to produce integrated circuits. In general, a lithography system, also referred to as an exposure system, typically includes an illumination system and a wafer positioning system. The illumination system includes a radiation source for providing radiation such as ultraviolet, visible, x-ray, electron, or ion radiation, and a reticle or mask for imparting the pattern to the radiation, thereby generating the spatially patterned radiation. In addition, for the case of reduction lithography, the illumination system can include a lens assembly for imaging the spatially patterned radiation onto the wafer. The imaged radiation exposes resist coated onto the wafer. The illumination system also includes a mask stage for supporting the mask and a positioning system for adjusting the position of the mask stage relative to the radiation directed through the mask. The wafer positioning system includes a wafer stage for supporting the wafer and a positioning system for adjusting the position of the wafer stage relative to the imaged radiation. Fabrication of integrated circuits can include multiple exposing steps. For a general reference on lithography, see, for example, J. R. Sheats and B. W. Smith, in *Microlithography: Science and Technology* (Marcel Dekker, Inc., New York, 1998), the contents of which is incorporated herein by reference.

Figure 14A:
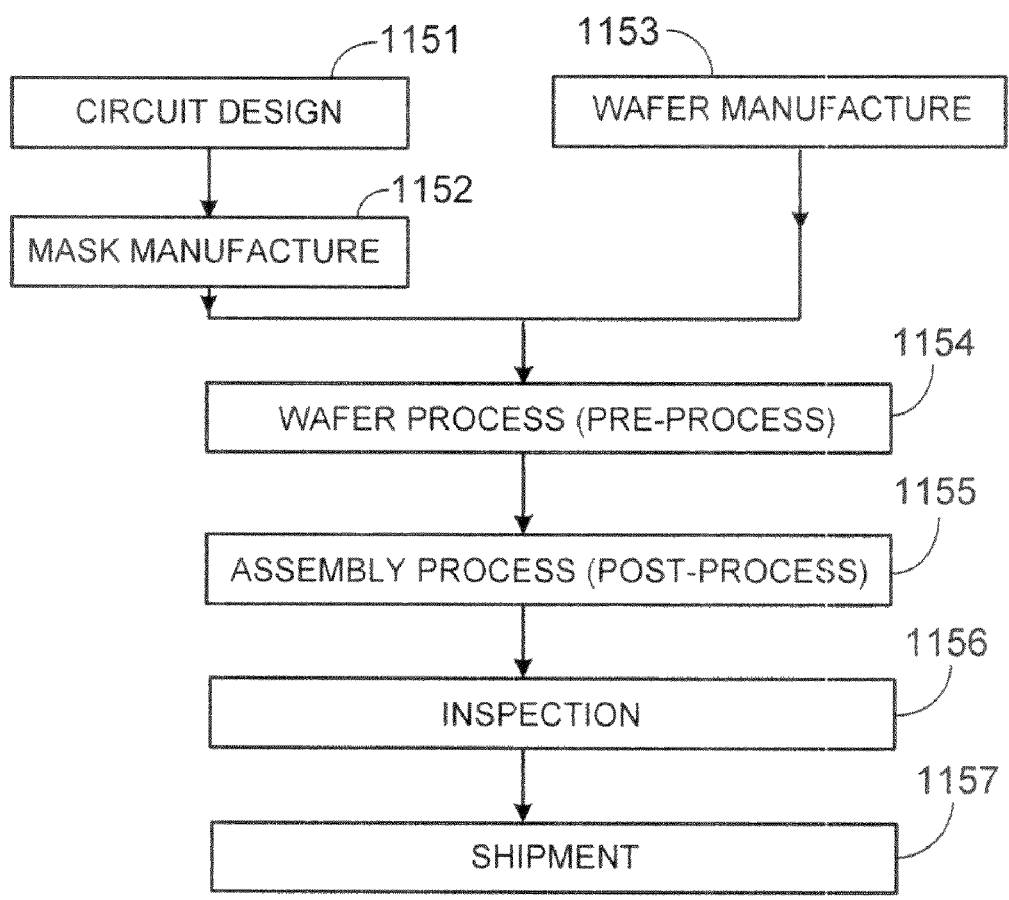
FIG. 14(a) and FIG. 14(b) are flow charts that describe steps for producing integrated circuits.

As is well known in the art, lithography is a critical part of manufacturing methods for making semiconducting devices. For example, U.S. Pat. No. 5,483,343 outlines steps for such manufacturing methods. These steps are described below with reference to FIGS. 14(a) and 14(b). FIG. 14(a) is a flow chart of the sequence of manufacturing a semiconductor device such as a semiconductor chip (e.g., IC or LSI), a liquid crystal panel or a CCD. Step 1151 is a design process for designing the circuit of a semiconductor device. Step 1152 is a process for manufacturing a mask on the basis of the circuit pattern design. Step 1153 is a process for manufacturing a wafer by using a material such as silicon.

Step 1154 is a wafer process which is called a pre-process wherein, by using the so prepared mask and wafer, circuits are formed on the wafer through lithography. To form circuits on the wafer, patterns from multiple masks are sequentially transferred to different layers on the wafer, building up the circuits. Effective circuit production requires accurate overlay between the sequentially formed layers. The interferometry methods and systems described herein can be especially useful to provide accurate overlay and thereby improve the effectiveness of the lithography used in the wafer process.

Step 1155 is an assembling step, which is called a post-process wherein the wafer processed by step 1154 is formed into semiconductor chips. This step includes assembling (dicing and bonding) and packaging (chip sealing). Step 1156 is an inspection step wherein operability check, durability check and so on of the semiconductor devices produced by step 1155 are carried out. With these processes, semiconductor devices are finished and they are shipped (step 1157).

Figure 14B:
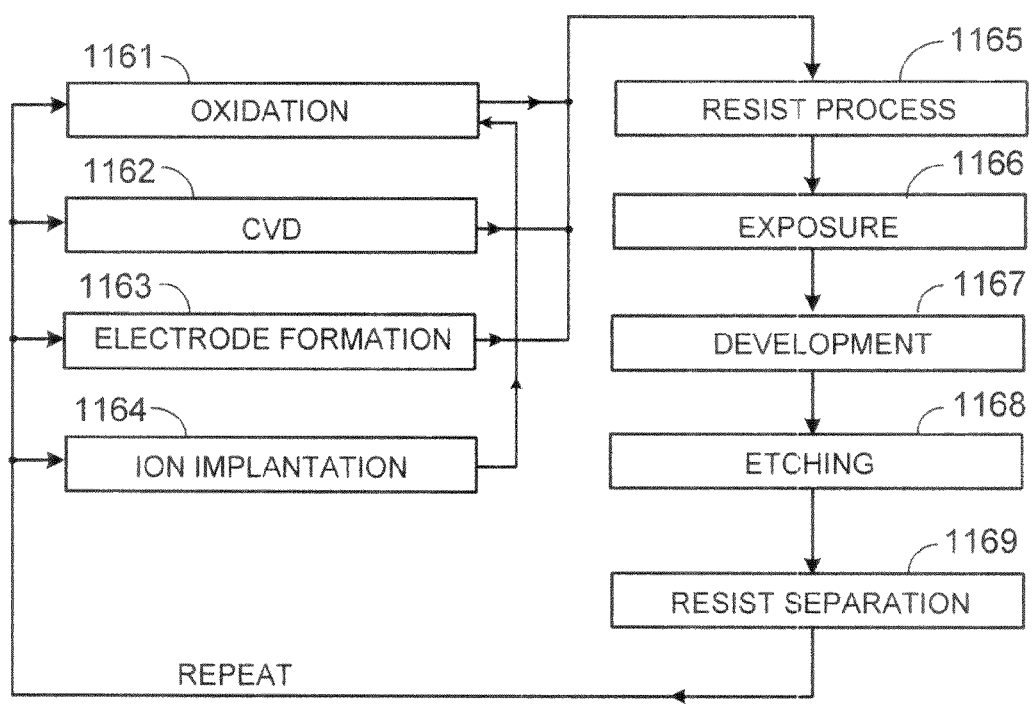

FIG. 14(b) is a flow chart showing details of the wafer process. Step 1161 is an oxidation process for oxidizing the surface of a wafer. Step 1162 is a CVD process for forming an insulating film on the wafer surface. Step 1163 is an electrode forming process for forming electrodes on the wafer by vapor deposition. Step 1164 is an ion implanting process for implanting ions to the wafer. Step 1165 is a resist process for applying a resist (photosensitive material) to the wafer. Step 1166 is an exposure process for printing, by exposure (i.e., lithography), the circuit pattern of the mask on the wafer through the exposure apparatus described above. Once again, as described above, the use of the interferometry systems and methods described herein can improve the accuracy and resolution of such lithography steps.

Step 1167 is a developing process for developing the exposed wafer. Step 1168 is an etching process for removing portions other than the developed resist image. Step 1169 is a resist separation process for separating the resist material remaining on the wafer after being subjected to the etching process. By repeating these processes, circuit patterns are formed and superimposed on the wafer.

As mentioned previously, the interferometry systems and methods disclosed herein can be used in the manufacture of flat panel displays such as, for example, liquid crystal displays (LCDs).

Figure 15:
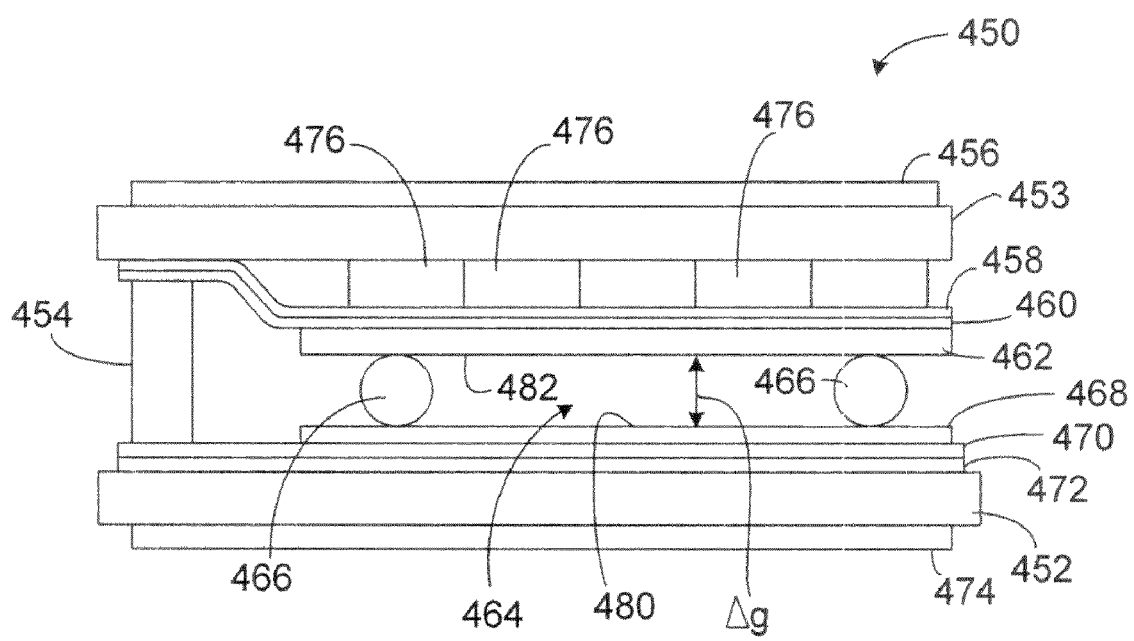
FIG. 15 is a schematic diagram of an embodiment of a LCD panel composed of several layers.

In general, a variety of different LCD configurations are used in many different applications, such as LCD televisions, desktop computer monitors, notebook computers, cell phones, automobile GPS navigation systems, automobile and aircraft entertainment systems to name a few. While the specific structure of a LCD can vary, many types of LCD utilize a similar panel structure. Referring to FIG. 15, for example, in some embodiments, a LCD panel 450 is composed of several layers including two glass plates 452,453 connected by seals 454. Glass plates 452 and 453 are separated by a gap 464, which is filled with a liquid crystal material. Polarizers 456 and 474 are applied to glass plates 453 and 452, respectively. One of the polarizers operates to polarize light from the display's light source (e.g., a backlight, not shown) and the other polarizer serves as an analyzer, transmitting only that component of the light polarized parallel to the polarizer's transmission axis.

An array of color filters 476 is formed on glass plate 453 and a patterned electrode layer 458 is formed on color filters 476 from a transparent conductor, commonly Indium Tin Oxide (ITO). A passivation layer 460, sometimes called hard coat layer, based on SiOx is coated over the electrode layer 458 to electrically insulate the surface. Polyimide 462 is disposed over the passivation layer 460 to align the liquid crystal fluid 464.

Panel 450 also includes a second electrode layer 472 formed on glass plate 452. Another hard coat layer 470 is formed on electrode layer 472 and another polyimide layer 468 is disposed on hard coat layer 470. In active matrix LCDs (AM LCDs), one of the electrode layers generally includes an array of thin film transistors (TFTs) (e.g., one or more for each sub-pixel) or other integrated circuit structures.

The liquid crystal material is birefringent and modifies the polarization direction of the light propagating through the material. The liquid crystal material also has a dielectric anisotropy and is therefore sensitive to electric fields applied across gap 464. Accordingly, the liquid crystal molecules change orientation when an electric field is applied, thereby varying the optical properties of the panel. By harnessing the birefringence and dielectric anisotropy of the liquid crystal material, one can control the amount of light transmitted by the panel.

The cell gap $\Delta g$, i.e., thickness of the liquid crystal layer 464, is determined by spacers 466, which keep the two glass plates 452,453 at a fixed distance. In general, spacers can be in the form of preformed cylindrical or spherical particles having a diameter equal to the desired cell gap or can be formed on the substrate using patterning techniques (e.g., conventional photolithography techniques).

In general, LCD panel manufacturing involves multiple process steps in forming the various layers. For example, referring to FIG. 16, a process 499 includes forming the various layers on each glass plate in parallel, and then bonding the plates to form a cell. The cell is then filled with the liquid crystal material and sealed. After sealing, the polarizers are applied to the outer surface of each of the glass plates, providing the completed LCD panel.

Figure 16:
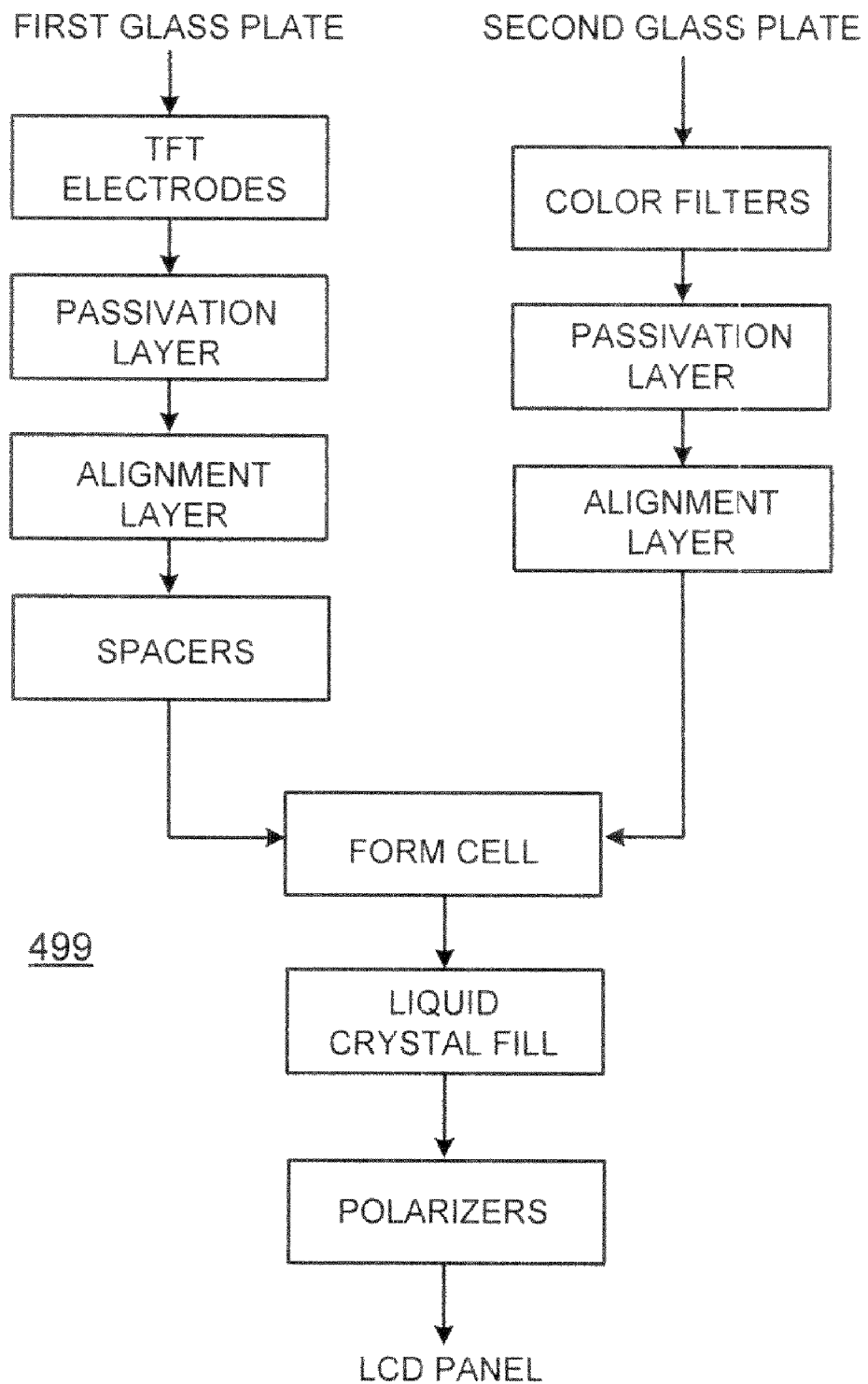
FIG. 16 is a flowchart showing various steps in LCD panel production.

In general, formation of each of the components illustrated in the flow chart in FIG. 16 can include multiple process steps. For example, in the present example, forming the TFT electrodes (commonly referred to as "pixel electrodes") on the first glass plate involves many different process steps. Similarly, forming the color filters on the second glass plate can involve numerous process steps. Typically, forming pixel electrodes include multiple process steps to form the TFTs, ITO electrodes, and various bus lines to the TFTs. In fact, forming the TFT electrode layer is, in essence, forming a large integrated circuit and involves many of the same deposition and photolithographic patterning processing steps used in conventional integrated circuit manufacturing. For example, various parts of the TFT electrode layer can be built by first depositing a layer of material (e.g., a semiconductor, conductor, or dielectric), forming a layer of photoresist over the layer of material, exposing the photoresist to patterned radiation. The photoresist layer is then developed, which results in a patterned layer of the photoresist. Next, portions of the layer of material lying beneath the patterned photoresist layer are removed in a etching process, thereby transferring the pattern in the photoresist to the layer of material. Finally, the residual photoresist is stripped from the substrate, leaving behind the patterned layer of material. These process steps can be repeated many times to lay down the different components of the TFT electrode layer.

In general, the interferometry techniques disclosed herein can be used to monitor overlay of different components of an LCD panel. For example, during panel production, the interferometry techniques can be used to determine overlay error between patterned resist layers and features beneath the photoresist layer. Where measured overlay error is outside a predetermined process window, the patterned photoresist can be stripped from the substrate and a new patterned photoresist layer formed.

Other embodiments are in the following claims.

What is claimed is:

1. A system comprising:
   an interferometer configured to direct test light to an overlay target and subsequently combine it with reference light to form an interference pattern, the test and reference light being derived from a common source;
   a multi-element detector positioned to detect the interference pattern;
   one or more optics to image the overlay target on the multi-element detector;
   a base arranged to position the overlay target relative to the one or more optics;
   a translation stage arranged to vary a distance between the overlay target and the one or more optics to vary the relative optical path length between the test and reference light when they form the interference pattern; and
   an electronic processor in communication with the multi-element detector,
   wherein the overlay target comprises a first pattern and a second pattern and the electronic processor is configured to acquire interferometric information from the multi-element detector while the translation stage varies the distance and to determine information about the relative alignment between the first and second patterns based on an asymmetry of fringes in the interference pattern in a direction across the multi-element detector indicative of the relative alignment,
   wherein the asymmetry of fringes is attributable to an asymmetry of phase of the interference pattern.

2. The system of claim 1, wherein the translation is stage is configured to move at least a portion of the interferometer relative to the base.

3. The system of claim 2, further comprising the common source, wherein the translation stage is configured to vary the optical path length over a range larger than a coherence length for the common source.

4. The system of claim 1, wherein the asymmetry corresponds to a deviation of an intensity profile of the interference pattern in the direction from a sinusoidal function.

5. The system of claim 1, wherein the first pattern is a periodic pattern in at least a first dimension.

6. The system of claim 5, wherein the first pattern is a grating having a first period.

7. The system of claim 6, wherein the second pattern is a grating having a second period.

8. The system of claim 7, wherein the first and second periods are the same.

9. The system of claim 6, wherein the first period is in a range from 50 nm to about 1,000 nm.

10. The system of claim 1, wherein the interferometer comprises a beam splitter configured to separate input light derived from the common source into the test light and the reference light, and a reference surface positioned to reflect the reference light before it is combined with the test light.

11. The system of claim 10, wherein test light is configured to reflect from the overlay target, and the beam splitter in the interferometer is positioned to recombine the test and reference light after they reflect from the respective test and reference surfaces.

12. The system of claim 1, wherein the common source is spatially extended.

13. The system of claim 1, further comprising the common source, wherein the common source is a broadband source spanning more than 50 nm at full width half maximum.

14. The system of claim 1, further comprising the common source, wherein the common source is a tunable source, the interferometer comprises a reference surface positioned to reflect the reference light, and the reference surface is further positioned to produce a non-zero optical path length difference with the test light at the interference pattern.

15. The system of claim 1, wherein the first pattern is formed in a first layer of the overlay target and the second pattern is formed in a second layer of the overlay target, the first layer being different from the second layer.

16. The system of claim 1, wherein the first and second patterns are formed in a single layer of the overlay target.

17. An interferometry method, comprising:
directing test light to an overlay target;
receiving the test light from the overlay target with an objective;
subsequently combining the test light with reference light to form an interference pattern, wherein the test and reference light are derived from a common source and the overlay target comprises a first layer having a first pattern and a second layer having a second pattern;
monitoring the interference pattern while varying an optical path difference between the test light and the reference light, where the optical path difference is varied by varying a distance between the overlay target and the objective; and
determining information about the relative alignment between the pattern of the first layer and the pattern of the second layer based on an asymmetry of fringes in the interference pattern in a direction across the multi-element detector indicative of the relative alignment,
wherein the asymmetry of fringes is attributable to an asymmetry of phase of the interference pattern.

18. The interferometry method of claim 17, wherein determining the information comprises determining a spatial frequency transform of the interference pattern.

19. The interferometry method of claim 18, wherein the transform is a Fourier transform.

20. The interferometry method of claim 17, wherein the method is performed using an imaging interferometer and the first and second patterns comprise features that are underresolved by the imaging interferometer.

21. The interferometry method of claim 17, wherein the information about the relative alignment is determined in two orthogonal dimensions using first and second patterns that are composed of structures that are periodic in the two dimensions.

22. A system comprising:
an interferometer configured to direct test light to an overlay target and subsequently combine it with reference light to form an interference pattern, the test and reference light being derived from a common source;
a multi-element detector positioned to detect the interference pattern;
an objective to direct the test light to the multi-element detector;
a base arranged to position the overlay target relative to one or more optics of the interferometer;
a translation stage arranged to vary a distance between the overlay target and the objective to vary the relative optical path length between the test and reference light when they form the interference pattern; and
an electronic processor in communication with the multi-element detector,
wherein the overlay target comprises a first pattern and a second pattern, the first and second patterns including features that are underresolved by the interferometer and the electronic processor is configured to acquire interferometric information from the multi-element detector while the translation stage varies the distance and to determine information about the relative alignment between the features of the first and second patterns based on an asymmetry of fringes in the interference pattern in a direction across the multi-element detector indicative of the relative alignment,
wherein the asymmetry of fringes is attributable to an asymmetry of phase of the interference pattern.

23. A process for making a display panel, comprising:
providing a component of the display panel, the component supporting an overlay target;
determining information about the overlay target using the system of claim 1; and
forming the display panel using the component based on the information about the overlay target.

24. A process for making an integrated circuit, comprising:
providing a substrate comprising one or more integrated circuit structures;
determining information about the one or more integrated circuit structures using the system of claim 1, where the substrate comprises the overlay target and the information is information about the overlay target; and
forming the integrated circuit using the substrate based on the information.

* * * * *